US008648232B2

(12) United States Patent
Ichikawa et al.

(10) Patent No.: US 8,648,232 B2
(45) Date of Patent: Feb. 11, 2014

(54) EARLY-MATURING TRANSGENIC PLANTS

(75) Inventors: Takanari Ichikawa, Yokohama (JP);
Mika Kawashima, Yokohama (JP);
Haruko Iizumi, Yokohama (JP);
Hirofumi Kuroda, Yokohama (JP);
Youichi Kondou, Yokohama (JP);
Motoaki Seki, Yokohama (JP); Yukako Hasegawa, Yokohama (JP); Minami Matsui, Yokohama (JP); Akie Ishikawa, Yokohama (JP); Miki Nakazawa, Yokohama (JP); Kumiko Suzuki, Yokohama (JP)

(73) Assignee: Riken, Wako-shi (JP)

( * ) Notice: Subject to any disclaimer, the term of this patent is extended or adjusted under 35 U.S.C. 154(b) by 556 days.

(21) Appl. No.: 12/281,265

(22) PCT Filed: Aug. 14, 2007

(86) PCT No.: PCT/JP2007/066080
§ 371 (c)(1),
(2), (4) Date: Oct. 28, 2008

(87) PCT Pub. No.: WO2008/020645
PCT Pub. Date: Feb. 21, 2008

(65) Prior Publication Data
US 2010/0058497 A1  Mar. 4, 2010

(30) Foreign Application Priority Data
Aug. 14, 2006 (JP) ................................. 2006-221061

(51) Int. Cl.
A01H 5/00 (2006.01)
A01H 5/10 (2006.01)
A01H 1/00 (2006.01)
C12N 15/82 (2006.01)

(52) U.S. Cl.
USPC ............ 800/298; 435/419; 800/278; 800/290

(58) Field of Classification Search
None
See application file for complete search history.

(56) References Cited

U.S. PATENT DOCUMENTS 5,981,841 A * 11/1999 Santino et al. ................ 800/298
6,225,530 B1 * 5/2001 Weigel et al. ................. 800/290

2002/0160378 A1  10/2002 Harper et al.
2004/0203013 A1  10/2004 Matsui et al.
2006/0075523 A1   4/2006 Kreps et al.

FOREIGN PATENT DOCUMENTS

| EP | 1033405 | 9/2000 |
|----|---------|--------|
| EP | 1 586 645 A2 | 10/2005 |
| WO | 02 16655 | 2/2002 |
| WO | WO 02/12518 A2 | 2/2002 |
| WO | 02 22675 | 3/2002 |
| WO | WO 02/12518 A3 | 10/2002 |
| WO | 03 008540 | 1/2003 |
| WO | 03 018808 | 3/2003 |
| WO | 2006 128921 | 12/2006 |

OTHER PUBLICATIONS

Bowie et al, Science 247:1306-1310, 1990.*
McConnell et al, Nature 411 (6838):709-713, 2001.*
Kano-Murakami et al (1993, FEBS 334:365-368).*
Barry J. MiCallef, et al. "Altered photosynthesis, flowering, and fruiting in transgenic tomato plants that have an increased capacity for sucrose synthesis", Planta, vol. 196, No. 2, XP000651658, Jan. 1, 1995, pp. 327-334.
Tomoko Endo, et al., "Ectopic expression of an *FT* homolog from *Citrus* confers an early flowering phenotype on trifoliate orange (*Poncirus trifoliata* L. Raf.)" Transgenic Research, vol. 14, No. 5, XP019269469, Oct. 1, 2005, pp. 703-712.
Danilo D. Fernando, et al., "Constitutive expression of the *SAP1* gene from willow (*Salix discolor*) causes early flowering in *Arabidopsis thaliana*", Development Genes and Evolution, vol. 216, No. 1, XP019427553, Oct. 14, 2005, pp. 19-28.
C. Von Schweinichen, et al., "Expression of a Plant Cell Wall Invertase in Roots of *Arabidopsis* leads to Early flowering and an Increase in Whole Plant Biomass", Plant Biology, vol. 7, No. 5, XP002568911, Sep., 2005, pp. 469-475.
Ichikawa T. et al., "The Fox Hunting system: an alternative gain-of-function gene hunting technique", The Plant Journal, vol. 45, pp. 974-985, (2006).
Fujimori T. et al., "Circadian-Controlled Basic/Helix-Loop-Helix Factor, PIL6, Implicated in Light-Signal Transduction in *Arabidopsis thaliana*", Plant Cell Physiol, vol. 45, No. 8, pp. 1078-1086, (2004).

* cited by examiner

Primary Examiner — Stuart F Baum
(74) Attorney, Agent, or Firm — Oblon, Spivak, McClelland, Maier & Neustadt, L.L.P.

(57) ABSTRACT

The present invention provides an early-maturing transgenic plant, which comprises a nucleic acid that encodes a protein having activity of causing early maturation of a plant, so that the gene can be expressed.

13 Claims, 9 Drawing Sheets

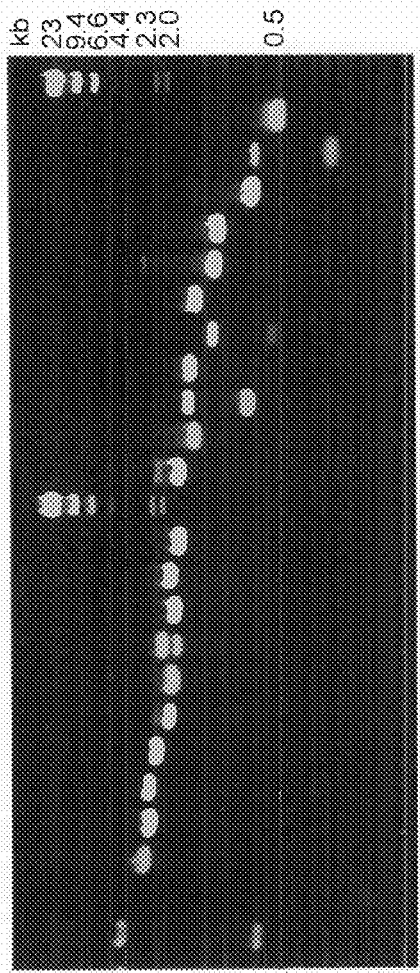
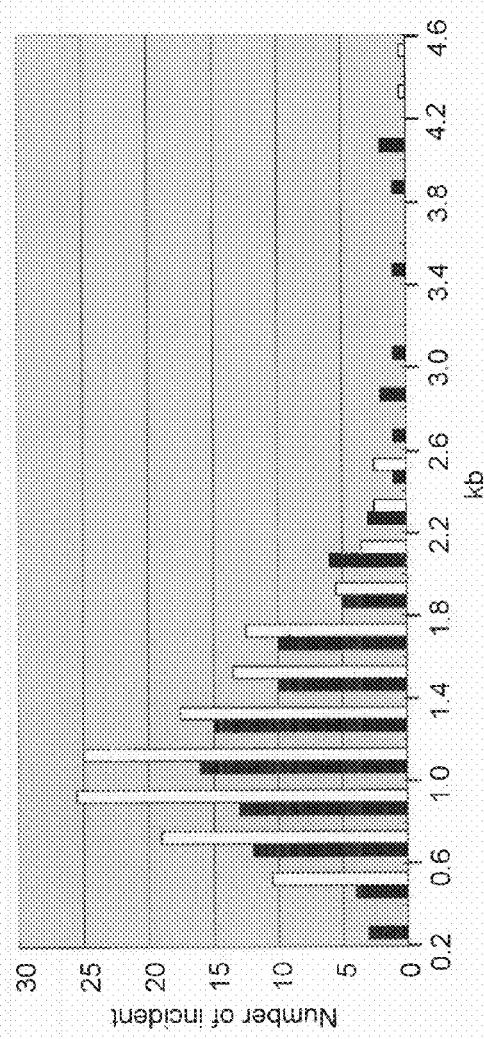
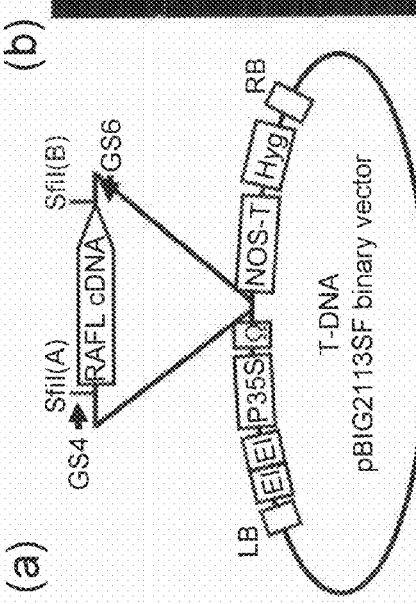
Fig. 1

Fig. 3
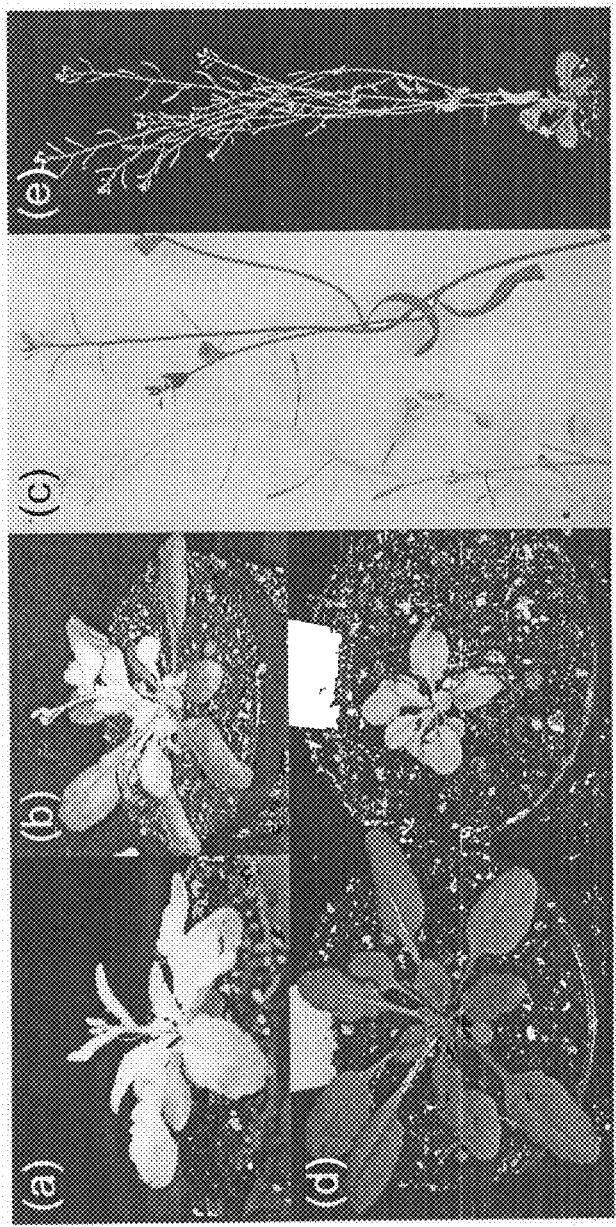
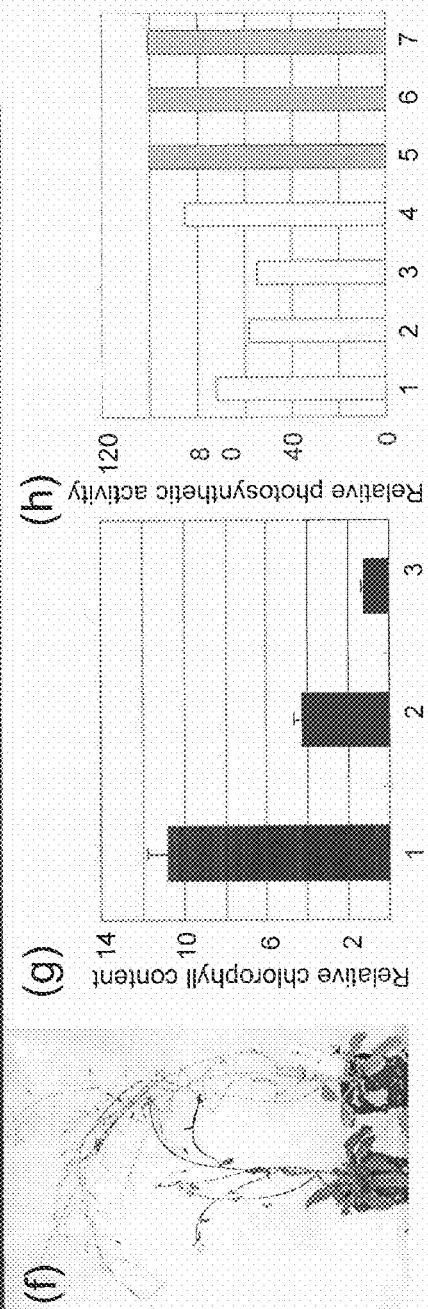

Fig. 6

Fig. 9
(a)
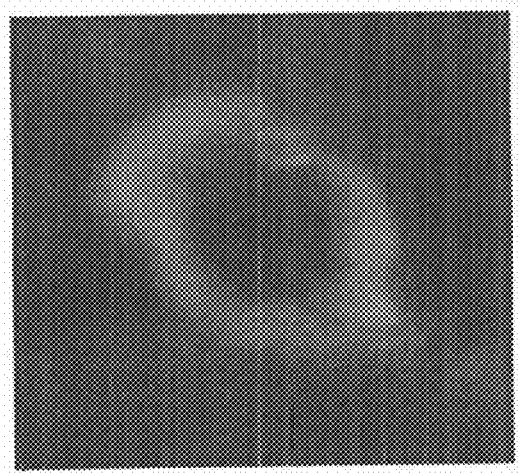
(b)
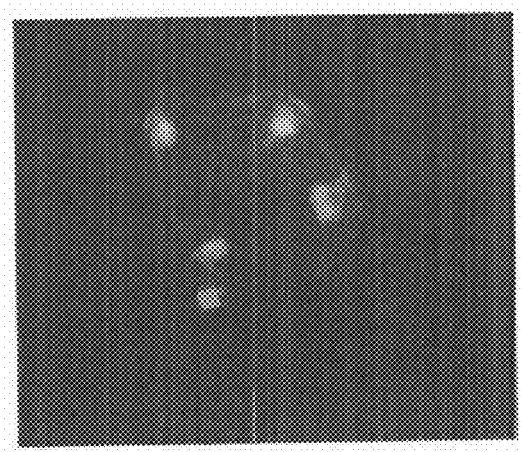

EARLY-MATURING TRANSGENIC PLANTS

CROSS-REFERENCE TO RELATED APPLICATIONS

The present application is a 35 U.S.C. §371 National Stage patent application of International patent application PCT/JP2007/066080, filed on Aug. 14, 2007, which claims priority to Japanese patent application JP 2006-221061, filed on Aug. 14, 2006.

TECHNICAL FIELD

The present invention relates to early-maturing transgenic plants, a method for producing the same, and a method for causing early maturation of plants.

BACKGROUND ART

An activation tagging method has been conventionally used as a method for analyzing gene functions. Such method involves producing a mutant with activated transcription of a plant gene with the use of a transcription enhancer sequence incorporated within T-DNA and then cloning the transcriptionally activated gene (Non-patent document 1). A gene that suppresses lateral root formation has been discovered with the use of this method (Patent document 1).

However, the activation tagging method is problematic for use in exhaustive analysis of gene functions (collective analysis of the functions of genes existing in the genome). For example, a 10-Kb genomic region contains an average of 2 or more genes in a model plant such as *Arabidopsis*. However, in the activation tagging method, an enhancer sequence is used as an activator within a tag and a transcriptionally activatable genomic region has a length of 5 Kb extending beyond each end of an insertion site. Hence, the effects of gene activation with the use of an enhancer are not limited to a single gene, but transcription of a plurality of genes is activated, so that composite phenotypes are generated (Non-patent document 2).

To avoid this problem, the present inventors have developed a technique called the "Fox hunting system (Full length cDNA over-expression gene hunting system)" (Patent document 2). The Fox hunting system is a method that involves introducing a full-length cDNA library as a gene source for strong expression directly in the form of a mixture into a plant through mediation with an *Agrobacterium* having a strong expression T-DNA vector, seeding the thus obtained $T_1$ seeds, and then screening for phenotypes. When a phenotype of interest appears, a full-length cDNA inserted into the relevant line is examined by PCR and sequencing, thereby resulting in identification of the causative gene.

Examples of the advantages of the Fox hunting system are as described below.

(i) A full-length cDNA library contains all of the amino acid information required for genes to be able to function, so that introduced genes can exhibit their full original functions. Thus, such a full-length cDNA library has much higher efficiency for expressing functions than a general cDNA library. Furthermore, all cDNA fragments are provided with original initiation codon and stop codon information, so that protein fusion is not required for expression and protein expression efficiency is high.

(ii) Even if a library of hundreds of millions of clones is used for infection, only 1 to 2 clones are introduced into a plant. Different clones are introduced into transgenic plants, so that fewer instances (roughly two) of confirmation are required for cDNA isolation and phenotypic traits.

(iii) With the use of a conventional cDNA library, all the mRNA molecules are replaced by cDNA molecules at their intact quantitative ratios. Hence, the proportions of cDNAs (e.g., structural protein gene groups that are expressed at high levels and signal transduction associated gene groups that are generally expressed at low levels) existing in such cDNA library differ significantly from each other depending on expression level. However, a library that can be used in the Fox hunting system is a "normalized" library that contains all clones in the same proportions regardless of gene expression level. The functions of genes of different species can be tested with efficiency higher than that of genome tagging (However, for plants such as *Arabidopsis* and rice for which normalized full-length cDNAs have already been established, such cDNAs may also be used. Moreover, when the functions of proteins with high expression levels, such as structural proteins, are analyzed, a general unnormalized full-length cDNA library may also be used).

(iv) The functions of all genes within a library can be searched without generating separate lines so as to prepare all plant populations containing full-length cDNAs. Hence, target mutants can be simply obtained and genes (whether or not the functions thereof are the original functions of such genes) imparting specific properties can be screened for with minimal effort.

Early maturation of plants has been reported as follows in Non-patent documents 3 and 4, for example.

At least in the case of *Arabidopsis* model plants, when a gene referred to as FT is activated within leaves, the mRNA thereof migrates via phloems to shoot apexes, thereby inducing flower buds. Accordingly, flower buds can be induced early via ectopic strong expression of the gene. However, the induction of flower buds requires intracellular gene expression following gene transfer via transformation, so that the preparation of a recombinant is also required herein. Furthermore, it is difficult to control the time during which the relevant gene is expressed; that is, the time during which flower formation is induced.

Patent Document 1: JP Patent Publication (Kokai) No. 2002-010786 A
Patent Document 2: JP Patent Republication (Saikohyo) No. 2003/018808
Non-patent Document 1: Walden, R et al., Plant Mol Biol, 1994, 26(5): pp. 1521-8
Non-patent Document 2: Ichikawa et al., Plant J, 2003, 36: pp. 421-429
Non-patent Document 3: Heang et al., Science 2005, 309, pp. 1694-1696
Non-patent Document 4: Hanzawa et al., PNAS 2005, 102, pp. 7748-7753

DISCLOSURE OF THE INVENTION

An object of the present invention is to discover a plant early maturing gene and then to provide a plant transformed with the gene.

The present inventors have generated approximately 15,000 *Arabidopsis* transformant lines using the above Fox hunting system and then observed lines with mutant phenotypes. Thus, the present inventors have discovered morphological mutants undergoing early maturation and succeeded in isolation of genes causing such mutation, thus completing the present invention.

Specifically, the present invention is as described below.

[1] An early-maturing transgenic plant, containing a nucleic acid that encodes:
(a) a protein comprising an amino acid sequence shown in SEQ ID NO: 2, 33, 35, or 37;
(b) a protein comprising an amino acid sequence comprising a deletion(s), substitution(s), or addition(s) of one or several amino acids in the amino acid sequence shown in SEQ ID NO: 2, 33, 35, or 37 and having activity of causing early maturation of a plant; or
(c) a protein comprising an amino acid sequence having 90% or more identity with the amino acid sequence shown in SEQ ID NO: 2, 33, 35, or 37 and having activity of causing early maturation of a plant; such that the nucleic acid can be expressed.

[2] The transgenic plant according to [1], wherein the nucleic acid contains:
(d) DNA comprising a nucleotide sequence shown in SEQ ID NO: 1, 32, 34, or 36;
(e) DNA comprising a nucleotide sequence comprising a deletion(s), substitution(s), or addition(s) of one or several nucleotides in the nucleotide sequence shown in SEQ ID NO: 1, 32, 34, or 36 and encoding a protein having activity of causing early maturation of a plant;
(f) DNA comprising a nucleotide sequence having 90% or more identity with the nucleotide sequence shown in SEQ ID NO: 1, 32, 34, or 36 and encoding a protein having activity of causing early maturation of a plant; or
(g) DNA hybridizing under stringent conditions to DNA complementary to DNA comprising a nucleotide sequence shown in SEQ ID NO: 1, 32, 34, or 36 and encoding a protein having activity of causing early maturation of a plant.

[3] The transgenic plant according to [1], wherein the plant is a dicotyledonous plant or a monocotyledonous plant.

[4] The transgenic plant according to [1], wherein the nucleic acid is incorporated in the plant genome.

[5] The transgenic plant according to [1], wherein the protein further has activity of increasing the size of a plant compared with that of a wild-type plant thereof.

[6] A tissue, cell or seed, which is derived from the transgenic plant according to any one of [1] to [5].

[7] A method for producing the early-maturing transgenic plant according to any one of [1] to [5], comprising introducing the nucleic acid defined in [1] or [2] into a plant tissue or cell and regenerating a plant.

[8] The method according to [7], wherein the introduction of the nucleic acid is carried out using a recombinant vector comprising the nucleic acid.

[9] A method for causing early maturation of a plant, comprising causing overexpression of the nucleic acid defined in [1] or [2] in the transgenic plant according to any one of [1] to [5], thereby inducing early maturation.

[10] A method for increasing the size of a plant, comprising causing overexpression of the nucleic acid defined in [1] or [2] in the transgenic plant according to any one of [1] to [5], thereby inducing an increase in plant size compared with that of a wild-type plant thereof.

[11] A method for causing early maturation of a plant, comprising applying the protein defined in [1] to soil or a plant to induce early maturation.

[12] A method for increasing the size of a plant, comprising applying the protein defined in [1] to soil or a plant to induce an increase in plant size compared with a wild-type plant thereof.

The term "nucleic acid" used in this description refers to DNA or RNA and examples of such nucleic acid include genes, cDNAs, mRNAs, and chemically modified products thereof.

This description includes part or all of the contents as disclosed in the description and/or drawings of Japanese Patent Application No. 2006-221061, which is a priority document of the present application.

BRIEF DESCRIPTION OF THE DRAWINGS

FIG. 1(a) shows a binary vector construct in which a full-length cDNA was introduced. FIG. 1(b) shows an electrophoretic image of amplified cDNA. FIG. 1(c) shows the size distribution of RAFL cDNA.

FIG. 2(a) shows a comparison between the iaaM over-expressing plant and a wild-type (WT) plant, which were grown for the same time period. FIG. 2(b) is a photograph showing the iaaM over-expressing plant. FIG. 2(c) is a photograph showing the tms1 over-expressing plant.

FIGS. 3(a) to (d) show the phenotypes of the F03024 line. FIGS. 3(e) to (f) show the phenotypes of the F01907 line. FIG. 3(g) shows the chlorophyll content of each line. FIG. 3(h) shows the photosynthetic activity of each line.

In FIG. 4(a), "19" and "21" denote PCR fragments specific to AtPDH1; "tubulin" denotes β-tubulin PCR fragments that were used as internal control genes; "lane 1" and "lane 2" denote wild-type Columbia plants; and "lane 3" and "lane 4" denote the F03024 plants exhibiting the pale green phenotype in the $T_2$ generation. In FIG. 4(b), the upper band denotes PCR fragments specific to At3g55240 and the lower band denotes AHA1 PCR fragments (AHA1: *Arabidopsis* plasma membrane H+-ATPase) used for loading adjustment. In FIG. 4(c), the upper band denotes the PCR fragments (p01907) specific to At3g55240, which was amplified by RT-PCR (the number of cycles: 40) and the lower band denotes PCR fragments of AHA1 (*Arabidopsis* plasma membrane H+-ATPase), which was amplified by RT-PCR (the number of cycles: 28) and used for loading adjustment.

FIG. 6 shows alignment of the AT3G55240 protein and the related proteins. AT3G55240 (SEQ ID NO: 2), AT3G28990 (SEQ ID NO: 33), and AT5G02580 (SEQ ID NO: 35) are *Arabidopsis* proteins and OS01G0837600 (SEQ ID NO: 37) (old name: P0031D11.2) is a rice EST protein.

FIG. 9(a) is a fluorescence microscopic image of *Arabidopsis* cultured cells expressing GFP. FIG. 9(b) is a fluorescence microscopic image of *Arabidopsis* cultured cells expressing a chimeric N98-GFP protein.

BEST MODE FOR CARRYING OUT THE INVENTION

Figure 2:
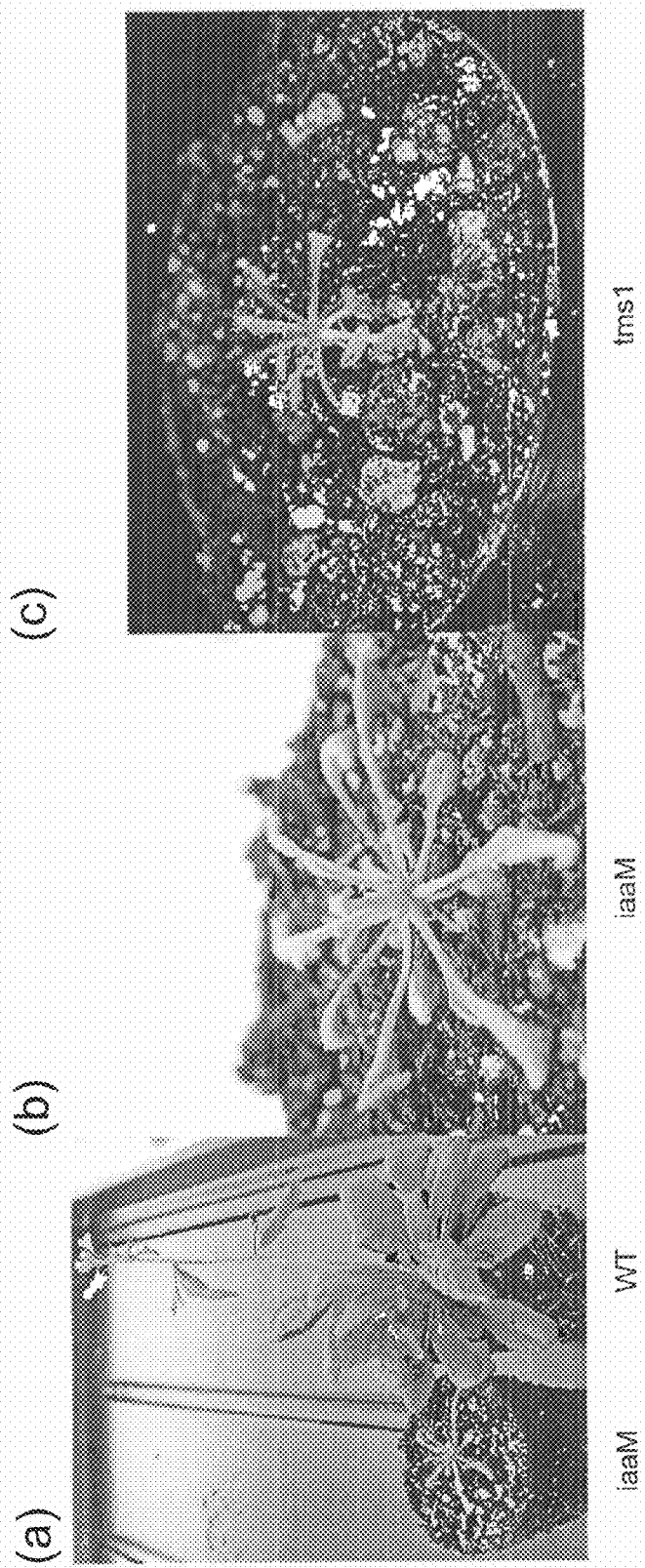
FIG. 2 shows over-expression phenotypes of oncogenes and a plant with wild-type phenotype observed using *Arabidopsis*.

1. Isolation of Plant Early Maturing Gene

A plant early maturing gene can be obtained by the Fox hunting system using *Arabidopsis*, for example. However, the following techniques are applicable not only for *Arabidopsis*, but also for other plants (and particularly, for Angiospermae).

Specifically, isolation of such a plant early maturing gene can be performed by the following procedures.

(1) Preparation of cDNA Mixture Containing Full-Length cDNA and Internal Control Gene The term "full-length cDNA" refers to DNA having the same sequence (however, wherein U→T) as that of mRNA transcribed from a gene; that is, a complete copy of mRNA. Even when a cDNA longer than the thus obtained cDNA is present, it can be an example of the full-length cDNA used herein.

Such full-length cDNA can be prepared from a target mRNA by a method known by persons skilled in the art. For example, a full-length cDNA can be prepared from mRNA derived from *Arabidopsis* by a technique such as a Cap-trapper method (Carninci, P., et al., Genomics, 1996. 37(3): pp. 327-36), or a Cap-finder method (Zhao, Z., et al., J. Biotechnol., 1999. 73(1): pp. 35-41). Moreover, an *Arabidopsis* full-length cDNA collection (RIKEN (Wako, Japan)) may also be used, in which the entire genomic cDNA has been sequenced.

An example of a vector for cloning of full-length cDNA that can be preferably used herein is a vector having a restriction enzyme site, such as Sfi I, capable of recognizing 8 or more nucleotides and defining a single direction of DNA to be inserted, on both ends of a cDNA insertion site.

A full-length cDNA library including the above full-length cDNAs can be constructed using a technique known by persons skilled in the art. Examples of a vector for construction of such library include Lambda Zap II, Lambda FLC-1-B, pTAS, and pBIG.

Furthermore, oncogenes (e.g., tms1, iaaM, rolB, and tmr) derived from bacteria may also be used as internal controls for later screening for phenotypes. The tms1 and iaaM genes encode tryptophan 2-monooxygenase derived from *Pseudomonas syringae* and the same derived from *Agrobacterium tumefaciens*, respectively. Overexpression of such genes results in production of auxin in a large quantity. The rolB gene is derived from *Agrobacterium rhyzogenesis* and is associated with auxin sensitivity. The tmr gene is derived from *Agrobacterium tumefaciens* and functions for cytokinin biosynthesis. These oncogenes are known to drastically affect many plants morphologically (Casanova et al., Biotechnol Adv, 23, 2005, 3-39; Romano et al., Plant Mol Biol, 27, 1995, 1071-83; Smart et al., Plant Cell, 3, 1991, 647-656). Such an oncogene can be used as an indicator for the uniformity of library cDNA. However, after transformation into *Arabidopsis*, these oncogenes are eliminated from mutant lines of the $2^{nd}$ generation. These oncogenes can be amplified by PCR.

(2) Normalization of Full-Length cDNA Library

As described in the background art, in a conventional cDNA library, the proportions of cDNA clones differ significantly from each other depending on gene expression level. Hence, it is preferable to perform "normalization" by which a library is constructed so as to contain all clones in the same proportions regardless of gene expression level.

A normalized full-length cDNA mixture can be obtained by mixing the equal amounts of full-length cDNA clones. To obtain such a normalized full-length cDNA mixture, the 5' terminal sequence and the 3' terminal sequence of the thus synthesized full-length cDNA are determined (single path sequencing), then non-redundant (sequences of partial regions at the termini are inconsistent) full-length cDNA clones are selected, and then a database of these clones is constructed.

The thus normalized full-length cDNA library is constructed by selecting cDNAs differing from each other and then mixing them in equal amounts. Hence, such a normalized full-length cDNA library does not include nonuniform molecular species as in the case of a conventional cDNA library, but rather, it is entirely uniform. Therefore, in view of also a multicopy gene group of genome genes, the functions of genes of different species can be tested with a greater degree of equality; that is, with higher efficiency than is possible with genome tagging.

In the case of *Arabidopsis*, normalized full-length cDNAs accounting for 50% or more of the total genome have been currently established and available. In the present invention, these available and normalized full-length cDNAs can be used.

(3) Cloning of Full-Length cDNA into Expression Vector

The thus obtained full-length cDNA or normalized full-length cDNA can be cloned into a T-DNA expression vector for plant transformation using *Agrobacterium tumefaciens*. T-DNA is a specific region of a Ti plasmid that is found in a pathogenic strain of *Agrobacterium*. (Agrobacterium is a pathogenic bacterium of a crown gall, which is a tumor of dicotyledonous plants.) When the bacterium infects a plant, T-DNA transfers into plant cells and then is incorporated into the genomic DNA.

The T-DNA contains a sequence for regulation of full-length cDNA expression. A cassette into which a promoter sequence capable of constantly or conditionally causing expression within plant cells and a terminator have been ligated is preferably incorporated as an expression regulatory sequence. An example of a preferable constant expression promoter sequence is a 35S promoter sequence of *Cauliflower Mosaic Virus* (Sanders, P. R. et al., Nucleic Acids Res, 1987. 15(4): pp. 1543-58). Examples of an inducible promoter include a glucocorticoid inducible promoter sequence (Aoyama, T. et al., Plant J, 1997. 11(3): pp. 605-12) and an estrogen inducible promoter sequence (Zuo, J et al., Plant J, 2000. 24(2): pp. 265-273). In the present invention, these promoters can be used in an arbitrary combination thereof (via ligation). Such combination of promoters may be comprised of constant expression promoters or inducible promoters. Furthermore, both types may be also used in combination.

Furthermore, for later plant selection, a hygromycin resistance gene may also be inserted, for example.

The above full-length cDNA or normalized full-length cDNA is inserted downstream of the promoter sequence in the sense or the antisense direction using T4 ligase, for example, via an enzyme reaction. Accordingly, a change that can be identified herein is: a change in a phenotypic trait resulting from overexpression of a gene encoding the relevant cDNA when the sense strand is expressed; or a change in a phenotypic trait resulting from underexpression of a gene encoding the relevant cDNA when the antisense strand is expressed.

(4) Introduction of Full-Length cDNA Library into Plant

Next, the above full-length or normalized full-length cDNA or a T-DNA population (Full-length cDNA over-expressor library; FOX library) in which an oncogene has been inserted is introduced into *Agrobacterium* by a standard method. After construction of a library, cDNAs within the library are introduced (transformed) into plants (e.g., *Arabidopsis*) via infection with *Agrobacterium*.

For infection of plants with *Agrobacterium*, a dipping method, a floral dipping method, and the like can be used. In the case of the dipping method, a bundle of plants is immersed in a liquid containing *Agrobacterium* for 30 to 60 seconds. In the case of the floral dipping method, flower buds of a plant host are directly immersed, pots are transferred onto trays, and then the pots are covered overnight to keep them moistened. The cover is removed on the next day, the plants are grown intact, and then seeds are harvested.

(5) Screening Based on Phenotypic Trait

Seeds are obtained from transgenic plants ($T_0$ generation) that have been produced by transformation of *Arabidopsis* plants and the like using an *Agrobacterium* FOX library. The seeds are then seeded on medium containing hygromycin, for example. Transgenic plants can be selected within approximately 1 week after budding, so that further culturing is not required for selection of hygromycin resistant seedlings. The thus selected plants ($T_1$ generation) are transferred onto soil, and then seeds are harvested.

(6) Reconfirmation of Phenotypic Trait and Identification of Gene Causing Mutant Trait Genomic DNA is extracted from transgenic plants of interest (e.g., plants having traits thought to relate to early maturation, such as plants undergoing early growth of their plants compared with other transgenic plants and plants undergoing early flowering). From the DNA, primers are designed based on the information of nucleotide sequences in the vicinity of the promoter sequence and the terminator sequence contained in T-DNA. Polymerase chain reaction (PCR) is performed using the primers and then the cDNA between the transcription regulatory regions is isolated. This cDNA is again inserted into T-DNA having a promoter sequence and a terminator sequence similar to those of the above, the T-DNA is re-introduced into a normal plant, and then the phenotypic traits are re-confirmed. Through the following cDNA sequencing, genes causing mutant traits can be identified.

2. Isolated and Identified Early Maturing Gene

The plant early maturing gene isolated and identified by the above technique is *Arabidopsis* At3g55240 (line name: F01907). Furthermore, examples of the early maturing gene in the present invention include *Arabidopsis* genes At3g28990, At5g02580, and rice EST Os01g0837600 (old name: P0031D11.2), each encoding a protein having activity of causing early maturation of a plant, which is equivalent to the activity of At3g55240. Moreover, proteins encoded by these genes have activity of increasing the size of a plant larger than that of a wild type plant thereof.

Here, the term "activity of causing early maturation of a plant" in the present invention refers to activity of accelerating the growth of a plant in which the early maturing gene is expressed compared with a wild-type plant thereof. Furthermore, the phrase "having activity of causing early maturation of a plant" refers to the fact that the activity is substantially equivalent to the activity of a protein having the amino acid sequence shown in SEQ ID NO: 2. Plants having such early maturing activity (or early maturing ability) are referred to as early maturing plants in this description.

Furthermore, the term "activity of increasing the size of a plant compared with a wild-type plant thereof" in the present invention refers to activity of increasing the size of a plant, such as height, compared with a wild-type plant corresponding thereto. Moreover, the phrase "having activity of increasing the size of a plant compared with a wild-type plant thereof" refers to the fact that the activity is substantially equivalent to the activity of a protein having the amino acid sequence shown in SEQ ID NO: 2.

The nucleotide sequence of At3g55240 is shown in SEQ ID NO: 1 and the amino acid sequence of the same is shown in SEQ ID NO: 2. The nucleotide sequence of At3g28990 is shown in SEQ ID NO: 32 and the amino acid sequence of the same is shown in SEQ ID NO: 33. The nucleotide sequence of At5g02580 is shown in SEQ ID NO: 34 and the amino acid sequence of the same is shown in SEQ ID NO: 35. The nucleotide sequence of Os01g0837600 (old name: P0031D11.2) is shown in SEQ ID NO: 36 and the amino acid sequence of the same is shown in SEQ ID NO: 37.

The above early maturing gene may be a gene encoding a protein that comprises an amino acid sequence comprising a deletion(s), substitution(s), or addition(s) of one or several amino acids in the amino acid sequence shown in SEQ ID NO: 2, 33, 35, or 37 and has activity of causing early maturation of a plant. Here the term "several" refers to an integer of approximately 10, 9, 8, 7, 6, 5, 4, 3, or 2. For example, 1 to 10, 1 to 8, and preferably 1 to 5 amino acids of the amino acid sequence shown in SEQ ID NO: 2, 33, 35, or 37 may be deleted, added, or substituted.

Furthermore, the above amino acid sequence may contain conservative amino acid substitution. Such substitution takes place between amino acids analogous to each other in terms of structural or electrical properties, for example. Examples of such amino acid groups include (1) acidic amino acid (aspartic acid and glutamic acid), (2) basic amino acid (lysine, arginine, and histidine), (3) nonpolar amino acid (alanine, valine, leucine, isoleucine, proline, phenylalanine, methionine, and tryptophan), (4) uncharged polar amino acid (glycine, asparagine, glutamine, cysteine, serine, threonine, and tyrosine), and (5) Aromatic Amino Acid (Phenylalanine and Tyrosinetryptophan).

Alternatively, the above early maturing gene may also be a gene encoding a protein that comprises an amino acid sequence having 70% or more identity with the amino acid sequence shown in SEQ ID NO: 2, 33, 35, or 37 and has activity of causing early maturation of a plant. Such identity is 70% or more, preferably 80% or more, 85% or more, more preferably 90% or more, and most preferably 95% or more. Here, the term "% identity" refers to the percentage of the number of the same amino acids with respect to the total number of amino acids in two aligned amino acid sequences. Such % identity can be determined using a homology search program such as BLAST or FASTA. Alignment can be performed in homology search by introducing or not introducing gaps. Moreover, GenBank, EMBL, or the like can be used as a sequence database, for example.

The above early maturing gene may be DNA comprising a nucleotide sequence shown in SEQ ID NO: 1, 32, 34, or 36.

Furthermore, the above early maturing gene may be DNA comprising a nucleotide sequence comprising a deletion(s), substitution(s), or addition(s) of one or several nucleotides in the nucleotide sequence shown in SEQ ID NO: 1, 32, 34, or 36 and encoding a protein having activity of causing early maturation of a plant. Here, the term "several" refers to an integer of approximately 10, 9, 8, 7, 6, 5, 4, 3, or 2.

Alternatively, the above early maturing gene may be DNA that comprises a nucleotide sequence having 70% or more, preferably 80% or more, 85% or more, more preferably 90% or more, and most preferably 95% or more identity with the nucleotide sequence shown in SEQ ID NO: 1, 32, 34, or 36 and encodes a protein having activity of causing early maturation of a plant. Here, the term "% identity" refers to the percentage of the number of the identical nucleotides with respect to the total number of nucleotides when two nucleotide sequences are aligned. Such % identity can be determined using a homology search program such as BLAST or FASTA. Alignment can be performed in homology search by introducing or not introducing gaps. Furthermore, GenBank, EMBL, or the like can be used as a sequence database.

Furthermore, the above early maturing gene may also be DNA that hybridizes under stringent conditions to DNA complementary to DNA comprising a nucleotide sequence shown in SEQ ID NO: 1, 32, 34, or 36 and encodes a protein having activity of causing early maturation of a plant. Here, the term "stringent conditions" refers to conditions under which namely specific hybrids are formed, but nonspecific hybrids are not formed. Such conditions comprise hybridization at approximately 45° C. using 5 to 6×SSC (sodium chloride/sodium citrate) and the following washing at approximately 50° C. to approximately 65° C. using 0.1 to 1×SSC and 0.1% SDS, for example. Alternatively, such conditions may also comprise hybridization at approximately 65° C. to approximately 70° C. using 1×SSC and the following washing at approximately 65° C. to approximately 70° C. using 0.3×SSC, for example.

A gene or DNA that can be prepared (altered) by a technique known in the art is a gene encoding a protein that comprises an amino acid sequence comprising a deletion(s), substitution(s), or addition(s) of one or several amino acids in the above amino acid sequence of SEQ ID NO: 2, 33, 35, or 37, a gene encoding a protein that has an amino acid sequence having 90% or more identity with the above amino acid sequence shown in SEQ ID NO: 2, 33, 35, or 37, DNA comprising a nucleotide sequence comprising a deletion(s), substitution(s), or addition(s) of one or several nucleotides in the above nucleotide sequence shown in SEQ ID NO: 1, 32, 34, or 36, DNA comprising a nucleotide sequence having 90% or more identity with the above nucleotide sequence shown in SEQ ID NO: 1, 32, 34, or 36, or DNA hybridizing under stringent conditions to DNA complementary to DNA comprising the above nucleotide sequence shown in SEQ ID NO: 1, 32, 34, or 36. Mutation can be introduced into a gene by a known technique such as the Kunkel method or the Gapped duplex method or a method according thereto. For example, mutation can be introduced using a kit for mutation introduction using site-specific mutagenesis (e.g., Mutant-K (produced by TaKaRa, Kyoto, Japan) or Mutant-G (produced by TaKaRa)) or a TaKaRa LA PCR in vitro Mutagenesis series kit. Moreover, site-specific mutagenesis may be employed, which is performed via PCR using primers into which mutation has been introduced (F. M. Ausubel et al., Short Protocols In Molecular Biology, 1995, third edition, John Wiliey&Sons, Inc.).

Once the nucleotide sequence of the above early maturing gene is determined, the early maturing gene can be obtained via chemical synthesis, PCR using as a template cloned cDNA, or hybridization using a DNA fragment having the nucleotide sequence as a probe.

Examples of a gene having high homology with the above early maturing gene include genes specified with the following accession Nos. of NCBI (National center for biotechnology information). Such genes and modified products thereof can also be used for producing the early-maturing transgenic plant of the present invention.

Rice: XM_475377.1
Maize: AY106962.1 GI: 21210040

3. Construction of Recombinant Vector and Production of Transgenic Plant (1) Construction of Recombinant Vector A recombinant vector to be used in the present invention can be constructed by inserting the above early maturing gene into an adequate vector. For example, pBI, pUC, and pTRA vectors are preferably used as vectors for introduction of the early maturing gene into plant cells and the following expression of the gene. A target gene can be introduced into a plant via Agrobacterium with the use of pBI and pTRA vectors. Such pBI binary vectors or intermediate vectors are preferably used and examples thereof include pBI121, pBI101, pBI101.2, and pBI101.3. With the use of pUC vectors, genes can be directly introduced into plants and examples thereof include pUC18, pUC19, and pUC9. Plant virus vectors, such as cauliflower mosaic virus (CaMV), bean golden mosaic virus (BGMV), and tobacco mosaic virus (TMV) vectors, can also be used.

A method employed herein for insertion of the early maturing gene into the vector involves first cleaving the purified DNA with an adequate restriction enzyme, inserting the resultant into the restriction enzyme site or multicloning site of an adequate vector DNA, and ligating the product to the vector, for example.

The early maturing gene needs to be incorporated into a vector such that functions of the gene are exhibited. Hence, a terminator, an enhancer, a selection marker, a splicing signal, a poly A additional signal, a 5'-UTR sequence, and the like can be ligated to the vector if desired, in addition to a promoter and the early maturing gene.

A "promoter" to be used herein may be DNA not derived from a plant, as long as the DNA can function in plant cells and can induce expression in a specific plant tissue or during a specific growth phase. Specific examples thereof include a cauliflower mosaic virus (CaMV) 35S promoter, a nopalin synthase gene promoter (Pnos), a maize ubiquitin promoter, a rice actin promoter, and a tobacco PR protein promoter.

Any "terminator" can be used as long as it comprises a terminator sequence that can terminate transcription of the gene transcribed by the above promoter. Specific examples thereof include a nopalin synthase gene terminator (Tnos) and a cauliflower mosaic virus polyA terminator.

A preferable example of an "enhancer" comprises an enhancer region that is used for improving the expression efficiency of a target gene and contains an upstream sequence in the CaMV 35S promoter.

Examples of a "selection marker" include a dihydrofolate reductase gene, an ampicillin resistance gene, a neomycin resistance gene, a hygromycin resistance gene, and a bialaphos resistance gene.

(2) Production of Early-Maturing Transgenic Plant

The early-maturing transgenic plant of the present invention can be obtained by introducing the above early maturing gene or a recombinant vector containing the same into a host so that the target gene can be expressed.

In the present invention, the term "transgenic plant" refers to a transgenic plant produced by gene manipulation and progeny plants thereof. Furthermore, examples of progeny plants include hybrid plants retaining ability of early maturation.

Transgenic plants can be obtained as follows.

Targets of transformation in the present invention are plant tissues (e.g., epidermis, phloem, parenchyma, xylem, and vascular bundle, and plant organs (e.g., leaves, petals, stems, roots, and seeds)) or plant cells.

Examples of plants to be used for transformation include, but are not limited to, dicotyledonous plants and monocotyledonous plants, such as plants (see the following examples) belonging to the family Brassicaceae, the family Gramineae, family Solanaceae, or the family Leguminosae.

The family Brassicaceae: Arabidopsis (*Arabidopsis thaliana*), rapeseed, cabbage, Chinese cabbage (*Brassica*), and the like.

The family Solanaceae: tobacco (*Nicotiana tabacum*), eggplant, potato (*Solaneum*), tomato (*Lycopersicon*), pepper (*Capsicum*), and the like.

The family Rosaceae: rose (*Rosa*), strawberry (*Fragaria*), cherry (*Prunus*), apple (*Malus*), and the like.

The family Asteraceae: Chrysanthemum (*Chrysanthemum*), sunflower (*Helianthus*), and the like.

The family Caryophyllaceae: carnation (*Dianthus caryophyllus*) and the like.

The family Gramineae: maize (*Zea mays*), rice (*Oryza sativa*), barley (*Hordeum*), wheat (*Triticum*), and the like.

The family Orchidaceae: *Cattleya* (*Cattleya*), *Phalaenopsis* (*Phalaenopsis*), and the like.

The family Liliaceae: Tulip (*Tulipa*) and the like.

The family Leguminosae: soybean (*Glycine max*), garden pea (*Pisum*), fava bean (*Vicia*), *Wisteria* (*Wisteria*), and the like.

Examples of a method for introducing the early maturing gene or a recombinant vector into plants include the *Agrobacterium* method, the PEG-calcium phosphate method, electroporation, the liposome method, the particle gun method, and microinjection. The *Agrobacterium* method may employ a protoplast or a tissue section. When a protoplast is employed, transformation can be performed by a method that involves culturing the protoplast together with an *Agrobacterium* having a Ti plasmid or a method that involves fusing a protoplast with a spheroplasted *Agrobacterium* (the spheroplast method), for example. When a tissue section is employed, transformation can be performed by a method (a leaf disc method) that involves causing an *Agrobacterium* to infect a leaf section (leaf disc) of an aseptically cultivated target plant or to infect a callus (undifferentiated cultured cells), for example. Moreover, acetosyringone can be used for transformation of a monocotyledonous plant by the *Agrobacterium* method, so as to increase the transformation rate.

Whether or not the gene has been incorporated into the plant can be confirmed via PCR, Southern hybridization, Northern hybridization, or other means. For example, DNA is prepared from a transgenic plant, a DNA-specific primer is designed, and PCR is then performed. After PCR has been performed, the amplification product is subjected to agarose gel electrophoresis, polyacrylamide gel electrophoresis, capillary electrophoresis, or the like and then stained with ethidium bromide, a SYBR Green solution, or the like, thereby detecting the amplification product as a band. Thus, transformation can be confirmed. Alternatively, the amplification product can also be detected via PCR with the use of a primer that has been previously labeled with a fluorescent dye or the like. Further, a method that may also be employed herein involves binding the amplification product to a solid phase such as a microplate to thereby confirm the amplification product via fluorescent reaction, enzyme reaction, or the like.

Tumor tissues, shoots, hairy roots, and the like obtained as a result of transformation can be directly used for cell culture, tissue culture, or organ culture. Furthermore, these transformation products can be regenerated into plants via a conventionally known plant tissue culture method that involves administration or the like of an adequate concentration of a plant hormone (e.g., auxin, cytokinin, gibberellin, abscisic acid, ethylene, or brassinolide). A plant is generally regenerated by causing roots to differentiate on medium in which appropriate types of auxin and cytokinin have been mixed, transplanting the resultants on medium having a high cytokinin content to cause shoot differentiation, and then transplanting the resultants in soil containing no hormone.

The thus obtained transgenic plant in which the above early maturing gene such as At3g55240 has been introduced exhibits an early maturing phenotype. Furthermore, such transgenic plant exhibits a phenotype of increasing plant size compared with that of a wild-type plant thereof. Moreover, *Arabidopsis* in which the At3g55240 gene has been introduced also possesses a phenotype of pale green coloration.

The term "early maturing" or "early maturation" in this description refers to a short growth period during which plants undergo seeding, flowering, maturation, and fructification.

The term "phenotype" in this description is used synonymously with "phenotypic trait." These terms represent easily observable or measurable plant morphological characteristics.

Plants with such early-maturing phenotypic traits can be harvested early, so that such traits are advantageous for reducing chances of exposure to disasters arising from the natural environment, such as typhoons. Moreover, the cultivation period, ranging from cultivation to delivery, can be considerably shortened in the case of ornamental plants having an early-maturing phenotypic trait, so that the costs of growing such plants can be significantly reduced. Furthermore, the phenotypic trait of increasing plant size compared with that of a wild-type plant thereof can increase biomass. Hence, such phenotypic trait is useful for plants that are to be used as industrial resources, for example.

The present invention further encompasses tissues, cells or seeds derived from the early-maturing transgenic plants of the present invention, which have been produced as described above. These tissues, cells or seeds also contain the nucleic acid or the early maturing gene of the present invention. In particular, such seeds make it possible to transfer the genotypes and traits thereof to progenies.

4. Production of Protein Encoded by Early Maturing Gene

The above several types of early maturing gene have a motif at the N-terminal site that binds to the membrane structure as analyzed with an algorithm called TargetP V1.0. In the case of the amino acid sequence shown in SEQ ID NO: 2, a sequence that may be transported and then excised later is predicted to be present at the $34^{th}$ amino acid residue from the N terminus. Moreover, in the case of the amino acid sequence shown in SEQ ID NO: 33, 35, or 37, a similar amino acid residue is present (see FIG. 6). A protein having such a partial amino acid sequence is thought to have activity of causing early maturation of plants and/or activity of increasing the size of a plant compared with that of a wild-type plant thereof.

Therefore, in the case of the amino acid sequence shown in SEQ ID NO: 2, amino acids thought to compose an active portion are found by the following calculating formula:

95 (all amino acids of SEQ ID NO: 2)−33 (cleaved at amino acid 34 from the N terminus)=62 amino acids.

Specifically, such an active portion ranges from amino acid residue 34 to amino acid residue 95. Hence, a peptide that is synthesized so as to contain at least the sequence will have the relevant activities. Similarly, in the case of the amino acid sequence shown in SEQ ID NO: 33, 35, or 37, a peptide that is synthesized so as to contain at least an amino acid sequence corresponding to the amino acid sequence ranging from positions 34 to 95 of SEQ ID NO: 2 will have the relevant activities.

The protein that is encoded by an early maturing gene can be obtained by ligating (inserting) the early maturing gene isolated in 1. above into a recombinant vector (e.g., plasmid DNA or phage DNA) that can be replicated in a host, introducing the vector into a host other than a plant host, such as preferably *Escherichia coli*, to obtain a transformant, culturing the transformant, and then collecting the protein from the culture product. The term "culture product" refers to a culture supernatant, a cultured cell or microorganism, or a disrupted product of the cultured cell or microorganism.

Examples of the aforementioned plasmid DNA include a plasmid derived from *Escherichia coli* (e.g. pBR322, pBR325, pUC118, pUC119, pUC18, pUC19 and pBluescript), a plasmid derived from *Bacillus subtilis* (e.g. pUB110 and pTP5), and a plasmid derived from yeast (e.g. YEp13 and YCp50). Examples of phage DNA include the λ phage (e.g. Charon4A, Charon21A, EMBL3, EMBL4, λgt10, λgt11, and λZAP). Furthermore, animal virus vectors such as a retrovirus and a vaccinia virus and insect virus vectors such as a baculovirus can also be used.

Examples of hosts other than plant hosts that can be employed include: bacteria belonging to the genus *Escherichia* such as *Escherichia coli*, the genus *Bacillus* such as *Bacillus subtilis*, the genus *Pseudomonas* such as *Pseudomonas putida*, and the genus *Rhizobium* such as *Rhizobium meliloti*; yeast such as *Saccharomyces cerevisiae* and *Schizosaccharomyces pombe*; animal cells such as COS cells and CHO cells; and insect cells such as Sf9 cells.

Where a bacterium such as *Escherichia coli* or *Bacillus subtilis* is used as a host, examples of *Escherichia coli* to be used herein include, but are not limited to, DH5α, HB101, and DH10B and an example of *Bacillus subtilis* is, but is not limited to, *Bacillus subtilis*. In such a case, a promoter is not particularly limited as long as it can express the gene of the present invention in a host such as *Escherichia coli*. For example, *Escherichia coli*-derived or phage-derived promoters can be employed, such as a trp promoter, a lac promoter, a $P_L$ promoter, and a $P_R$ promoter. Preferably the aforementioned recombinant vector is capable of autonomously replicating in the bacterium and, at the same time, is also comprised of the above promoter, a ribosome binding sequence, the above early maturing gene, and a transcription termination sequence. Further, such recombinant vector may also be comprised of a gene for controlling a promoter. A method for introducing a recombinant vector into a bacterium is not particularly limited, as long as it is a method for introduction of DNA into a bacterium. For example, a method involving the use of calcium ions (Cohen, S, N. et al., Ploc. Natl. Acad. Sci., U.S.A., 69: 2110, 1972) and electroporation can be employed.

Where yeast is used as a host, *Saccharomyces cerevisiae* or *Pichea pastris* is used, for example. In this case, a promoter is not particularly limited as long as it can express the gene of the present invention in yeast. For example, a gal1 promoter, a gal10 promoter, a heat shock protein promoter, a MFα1 promoter, a PHO5 promoter, a PGK promoter, a GAP promoter, an ADH promoter, or an AOX1 promoter can be employed. A method for introducing a recombinant vector into yeast is not particularly limited, as long as it allows the introduction of DNA into yeast, and examples of such methods include electroporation, the spheroplast method, and the lithium acetate method.

Where an animal cell is used as a host, a monkey COS-7 cell, Vero, a Chinese hamster ovary cell (a CHO cell), a mouse L cell, or the like is used. In such a case, an SRα promoter, an SV40 promoter, an LTR promoter, a CMV promoter, or the like is used, and an early gene promoter of human cytomegalovirus may also be used, for example. Examples of methods for introducing a recombinant vector into an animal cell include electroporation, the calcium phosphate method, and lipofection.

Where an insect cell is used as a host, an Sf9 cell or the like is used. In this case, a promoter to be used herein is a polyhedron promoter, a P10 promoter, an *Autographa californica* polyhedrosis basic protein promoter, a baculovirus immediate early gene 1 promoter, or a baculovirus 39K late early gene promoter. Examples of methods for introducing a recombinant vector into an insect cell include the calcium phosphate method, lipofection, and electroporation.

The aforementioned methods for culturing transformants are performed in accordance with a general technique employed for culturing a host.

As a medium for culturing a transformant obtained using a microorganism host such as *Escherichia coli* or yeast, either a natural or synthetic medium may be used as long as it contains carbon sources, nitrogen sources, and inorganic salts assimilable by the microorganism and enables efficient culturing of the transformant. Examples of carbon sources include: carbohydrates such as glucose, fructose, sucrose, and starch; organic acids such as acetic acid and propionic acid; and alcohols such as ethanol and propanol. Examples of nitrogen sources include: ammonia; ammonium salts of inorganic or organic acids such as ammonium chloride, ammonium sulfate, ammonium acetate, and ammonium phosphate; other nitrogen-containing compounds; peptone; meat extract; and corn steep liquor. Examples of inorganic substances include: monopotassium phosphate, dipotassium phosphate, magnesium phosphate, magnesium sulfate, sodium chloride, iron(I) sulfate, manganese sulfate, copper sulfate, and calcium carbonate. Culture is generally carried out under aerobic conditions such as shaking culture or aeration agitation culture at 37° C. The pH is adjusted with an inorganic or organic acid, an alkali solution, or the like. During the culture, an antibiotic such as ampicillin or tetracycline may be added to the medium, if necessary.

When a microorganism transformed with an expression vector containing an inducible promoter is cultured, an inducer may be added to the medium, if necessary. For example, when a microorganism transformed with an expression vector containing a promoter that is inducible by isopropyl-β-D-thiogalactopyranoside (IPTG) is cultured, IPTG or the like may be added to the medium. When a microorganism transformed with an expression vector containing a trp promoter that is inducible by indoleacetic acid (IAA) is cultured, IAA or the like may be added to the medium.

Examples of a medium for culturing a transformant obtained using an animal host cell include generally used RPMI 1640 medium, DMEM medium, and such a medium supplemented with fetal bovine serum or the like. Generally, culture is carried out in the presence of 5% $CO_2$ at 37° C. for 1 to 30 days. During the culture, an antibiotic such as kanamycin or penicillin may be added to the medium, if necessary.

If the above protein is produced in the relevant microorganism or cell after the culture, the protein is collected by disrupting the cultured microorganism or cell via ultrasonication, repeated freeze-thaw cycles, processing with a homogenizer, or the like. If the protein is produced and secreted outside of the microorganism or cell, the culture fluid may be used in that state or subjected to centrifugation or another procedure to remove the microorganism or cell. Thereafter, general biochemical techniques for isolating/purifying a protein such as ammonium sulfate precipitation, gel chromatography, ion exchange chromatography, or affinity chromatography, are employed independently or in an appropriate combination to isolate and purify the protein from the above culture product.

In addition to the employment of the above gene recombination techniques, the protein used in the present invention or a peptide having the activity thereof can also be synthesized via cell-free protein synthesis in a wheat germ extract, an *Escherichia coli* extract, or a rabbit reticulocyte extract, for example (JP Patent Publication (Kokai) No. 10-80295 A (1998)).

5. Method for Causing Early Maturation of Plant and/or Increasing Plant Size The aforementioned protein or a peptide having the activity thereof, which is prepared as described in 4 above is applied to plants or soil (dusted, sprayed, or the like), so as to be able to cause early maturation of plants and/or increase the size of a plant compared with that of a wild-type plant thereof. Among peptides, a peptide comprising 62 amino acids in the amino acid sequence of SEQ ID NO: 2 is particularly thought to compose an active portion following the cleaved sequence. This is a hydrophilic peptide comprising only 62 amino acids and thus is thought to be easily soluble in water. The same applies to the corresponding amino acids in the amino acid sequence of SEQ ID NO: 33, 35, or 37. Therefore, roots can be caused to effectively absorb the protein or the peptide by mixing the protein or the peptide with water and then spraying the solution over the shoot apex or dissolving the protein or the peptide in water and then adding the solution to soil or an aqueous solution for cultivation.

Moreover, it can be said that another advantage of the above protein and the above peptide is that they are eco-friendly bioactive substances. This is because unlike chemical substances, such peptidic active substances are easily degraded in the natural environment and can be topically sprayed.

Inducers of plant early maturation or inducers of plant size increase comprising the above protein or the above peptide as an active ingredient can be produced containing a combination of the above protein or the above peptide with other ingredients useful for plant growth, such as carriers and additives that are generally used in the field of agriculture.

The dosage forms of the above inducers may be solid preparations (e.g., pellets, granular formulations, granules, powder materials, water dispersible powders, or granular water-dispersible powders) or liquid preparations (e.g., liquid drugs or emulsions). However, the examples are not limited thereto.

The content of the above protein or the above peptide is not particularly limited, as long as it is effective for causing early maturation of and/or increasing the size of a target plant. The active ingredient is contained so that the content ranges from 2% by weight to 60% by weight in the case of solid preparations or ranges from approximately 0.1 ppm to 10 ppm in terms of concentration for spraying in the case of liquid preparations, for example.

Examples of carriers in the case of solid preparations include mineral carriers such as kaolin clay, diatomaceous earth, bentonite, zeolite, calcium silicate, acid clay, activated clay, and Attapulgus clay, ammonium salts such as ammonium sulfate and ammonium chloride, phosphates such as dibasic potassium phosphate, carbonates such as sodium carbonate, sodium bicarbonate, and calcium carbonate, saccharides such as dextrose, fructose, sucrose, lactose, and dextrin, and water-soluble carriers such as urea, sodium chloride, sodium sulfate, polyethylene glycol that is in a solid form at normal temperature. Examples of carriers in the case of liquid preparations include water, phosphate buffer solutions, Tris buffer solutions, and citrate buffer solutions. The content of such a carrier ranges from, but is not particularly limited to, 5% by weight to 40% by weight in the case of solid preparations and ranges from 80% to 99% in the case of liquid preparations, for example.

Furthermore, as an additive, a dispersant, an expander, a binder, a lubricant additive, a surfactant, a diluent, or the like may also be added.

The above inducers can be produced by a known method. For example, a powder material can be produced by spray-drying a suspension containing the above protein or the above peptide, water, and if necessary a dispersant, a carrier, and the like. Moreover, for example, a liquid drug can be produced by dissolving the above protein or the above peptide in water or a buffer solution and then adequately adding an additive and the like.

A method for causing early maturation of and/or increasing the size of a plant is also provided according to the present invention, comprising causing overexpression of a plant early maturing gene in the above transgenic plant and thus inducing early maturation of a plant and/or an increase in the size of a plant compared with a wild-type plant thereof.

A method for causing overexpression of an early maturing gene is performed via administration of a substance to a growing plant, provision of environmental stress, or the like.

EXAMPLES

Example 1

The present invention is hereafter described in greater detail with reference to the following examples, although the present invention is not limited thereto.
1. Methods
(1) Preparation of cDNA Mixture Comprised of Normalized Full-Length cDNAs and Marker Genes

*Arabidopsis* (*Arabidopsis thaliana* Columbia strain) full-length cDNA libraries were constructed using the following two vectors. The vector Lambda Zap II (Stratagene, La Jolla, U.S.A.) was used for libraries RAFL2 to RAFL6 (RAFL: RIKEN *Arabidopsis* full-length cDNA clone). The vector Lambda FLC-1-B (Stratagene, La Jolla, U.S.A.) was used for libraries RAFL7 to RAFL11.

Clones from these libraries were single-pass sequenced (Seki et al., 2002, Plant J, 31, 279-92) to select non-redundant clones and to prepare a full-length cDNA mixture comprising approximately 15,000 cDNA clones at an average final concentration of 14 ng/ml for each clone.

It is known from the RAFL clone sequencing project (Yamada et al., 2003, Science 31 Oct. 2003: Vol. 302. no. 5646, pp. 842-846) that approximately one third of these clones contain one redundant cDNA. Thus this clone mixture comprises approximately 10,000 non-redundant full-length cDNA species.

The orientation of the full-length cDNA relative to the Sfi I cloning sites in the RAFL2 and RAFL3 libraries (corresponding to 1,623 clones in total) was opposite to those of the rest of the RAFL clones. In order to have an internal control for morphological screening, 4 bacterial genes relating to auxin synthesis (tms1, iaaM) (Comai et al., 1982, J Bacteriol, 149, 40-6; Klee et al., 1984, Proc Natl Acad Sci U.S.A., 81, 1728-32), auxin sensitivity (rolB) (Furner et al., 1986, Nature, 319, 422-427), and cytokinin synthesis (tmr) (Lichtenstein et al., 1984, J Nol Appl Genet, 2, 354-62) were amplified by PCR and then cloned into the Sfi I site of a pBluescript-derived vector. Each internal control plasmid was added separately to the full-length cDNA mixture at a concentration of 30 ng/ml. DNA templates and PCR primers used for the amplification of the internal control genes are as follows.

```
pT281 (tms1):
5'-AGAGGCCAAATCGGCCATGTCAGCTTCACCTCTCCTT-3'       (SEQ ID NO: 3)

5'-AGAGGCCCTTATGGCCCTAATTTCTAGTGCGGTAGTTAT-3'     (SEQ ID NO: 4)

pCP3 (iaaM):
5'-AGAGGCCAAATCGGCCATGTATGACCATTTTAATTCACCC-3'    (SEQ ID NO: 5)

5'-AGAGGCCCTTATGGCCCTAATAGCGATAGGAGGCGTTG-3'      (SEQ ID NO: 6)

pLJ-1 (rolB):
5'-TCCTCTAGAGGCCAAATCGGCCATGGATCCCAAATTGCTATTCCT-3'  (SEQ ID NO: 7)

5'-TGATCTAGAGGCCCTTATGGCCTTAGGCTTCTTTCTTCAGGTTTA-3'  (SEQ ID NO: 8)

pT281 (tmr):
5'-AGAGGCCAAATCGGCCATGGACCTGCATCTAATTTTCG-3'      (SEQ ID NO: 9)

5'-AGAGGCCCTTATGGCCCCTAATACATTCCGAACGGATGA-3'     (SEQ ID NO: 10)
```

(2) Construction of *Agrobacterium* Library of the Normalized Full-Length cDNAs

The cDNA mixture prepared in (1) above was digested with Sfi I (Takara Bio) and cloned into the Sfi I site of an *Agrobacterium* binary vector pBIG2113SF using T4 ligase (New England BioLabs, Beverly, U.S.A.). The pBIG2113SF vector is derived from pBIG2113N (Taji et al., 2002, Plant J, 29, 417-26) was used herein and two Sfi I sites were inserted into the Xba I site of pBIG2113N so that the full-length cDNA was inserted in a sense orientation relative to the 35S promoter.

FIG. 1(a) shows an example of a binary vector. "El" denotes the 5'-upstream sequence (−419 to −90) of a CaMV 35S promoter, "P35S" denotes a CaMV 35S promoter (−90 to −1), "Ω" denotes the 5'-upstream sequence of TMV, "NOS-T" denotes the polyadenylation signal of the nopaline synthetase gene of a Ti plasmid, and "Hyg" denotes a hygromycin resistance gene. Arrows indicate the positions of a GS4 primer and a GS6 primer, respectively, which are used for collecting cDNA.

Ligation was set up with a 6-fold molar excess of pBluescript with respect to a binary vector. *E. coli* DH10B (Invitrogen) was transformed with the ligation product by electroporation. Colonies were then mixed to isolate a plasmid library.

*Agrobacterium* GV3101 was transformed with the plasmid library by electroporation. The resulting bacterial colonies were mixed to construct an *Agrobacterium* library.

(3) Transformation and Growth of Plants

Transformation and growth of plants are as described in a previous report (Ichikawa et al., 2003, Plant J, 36, 421-429).

Short wild-type *Arabidopsis* (Col-0) and the transformed lines were grown at 22° C. in a cultivation container system (Arasystem, Gent, Belgium) under long day conditions (16 hours of light and 8 hours of dark periods). Wild-type plants were transformed by floral dipping using the *Agrobacterium* library (Clough et al., 1998, Plant J, 16, 735-43).

Hygromycin-resistant $T_1$ seedlings were selected for 7 days on basic agar medium (BAM) containing 50 mg/l hygromycin and then transferred to soil (Nakazawa et al., 2003, Biotechniques, 34, 28-30). Visible phenotypes (e.g., growth rate, plant color, flowering time, and change in fertility) were scored, all plants exhibiting the phenotype (FT1P) were transferred to new Arasystem trays, and then they were observed. Either rosette leaves or flowers were harvested from all of the FT1P plants for DNA analysis.

(4) DNA Gel-Blot Analysis and Hygromycin Resistance Test

Southern blotting was performed as described in a previous report (Meyer et al., 1995, Mol Gen Genet, 249, 265-73). Twenty (20) lines were randomly chosen and $T_2$ plants were grown in soil for 3 weeks under conditions similar to conditions described in the above (3) Transformation and growth of plants. Leaves were harvested from 3 plants per line and then homogenized in liquid nitrogen.

Genomic DNA was isolated according to the instruction manual using a DNeasy plant mini kit (Qiagen, Tokyo, Japan). A 0.5 kb PCR fragment amplified from pBIG2113SF, containing a part of the hygromycin resistance gene, was labeled using a DIG DNA Labeling Mix (F. Hoffmann-La Roche, Basel, Switzerland).

PCR primers for the DNA template used herein are as follows.

```
HN: 5'-ATGAAAAAGCCTGAACTCACCG-3'    (SEQ ID NO: 11)

HC: 5'-TCGAGAGCCTGCGCGACG-3'        (SEQ ID NO: 12)
```

Hybridization was performed according to the instruction manual except that it was performed with a probe concentration of 5 ng/ml at 44° C. using a solution (5×SSC, 50% formamide, 0.1% N-lauroylsarcosine, 0.02% SDS, 2% blocking reagent (F. Hoffmann-La Roche, Basel, Switzerland)) and that the second washing was performed using a solution of 0.1×SSC and 0.1% SDS.

Chemiluminescence was detected by LumiVisionPRO (Aisin) after the hybridized membrane had been treated with a DIG Nucleic Acid Detection Kit (F. Hoffmann-La Roche, Basel, Switzerland).

(5) Amplification and Cloning of Full-Length cDNA from FT1P Plants

Approximately 200 mg (fresh weight) of rosette leaves or flowers were harvested.

Five (5) ceramic particles (CERAMICS YTZ ball, D: 2.3 mm, Nikkato, Japan) and 300 µl of lysis buffer were added to the plant material and then the resultant was homogenized using Shake Master (Shake Master ver.1.0, Bio Medical Science, Tokyo, Japan). Genomic DNA was extracted using the Wizard Magnetic 96 DNA Plant System (Promega, Tokyo, Japan). A workstation system (Tecan genesis workstation 150, Tecan, Tokyo, Japan) was adopted to run the extraction protocol described in the extraction kit.

The following primers were used for cDNA PCR upon cloning into the Gateway vector.

```
B1GS7:
                                        (SEQ ID NO: 13)
5'-GGGGACAAGTTTGTACAAAAAAGCAGGCTCTAGAGGCCCTTATGGCC

G-3'

B2GS8:
                                        (SEQ ID NO: 14)
5'-GGGGACCACTTTGTACAAGAAAGCTGGGTTCGAGTTAATTAAATTAA

TCCCCC-3'
```

The following primer pair was used upon cloning into the pBIG2113SF vector.

```
GS4:
5'-ACATTCTACAACTACATCTAGAGG-3'    (SEQ ID NO: 15)

GS6:
5'-CGGCCGCCCCGGGGATC-3'           (SEQ ID NO: 16)
```

The PCR conditions for short fragments were comprised of 94° C. for 30 seconds for denaturation, 62° C. for 30 seconds for annealing, and 72° C. for 120 seconds for elongation. The PCR conditions for long fragments were comprised of 94° C. for 30 seconds for denaturation, 58° C. for 30 seconds for annealing, and 68° C. for 180 seconds for elongation. In both cases, the DNA was denatured prior to the reactions by 8 minutes of treatment at 95° C.

(6) Cloning of PCR Fragments into the Expression Vectors and Sequencing

The Gateway vector PCR fragments were first cloned into the pDONR-207 vector by BP clonase according to the instruction manual (Invitrogen, Carlsbad, U.S.A.). Inserted full-length cDNA fragments were sequenced using the following attL1 and attL2 primers.

```
attL1:
5'-TCGCGTTAACGCTAGCATGGATCTC-3'    (SEQ ID NO: 17)

attL2:
5'-GTAACATCAGAGATTTTGAGACAC-3'     (SEQ ID NO: 18)
```

For cloning into pBIG2113SF, the PCR fragments from $T_1$ plants were digested with Sfi I and then cloned into the Sfi I site of the vector. The thus obtained construct was named pF01907 in the case of the F01907 line, for example. Inserted full-length cDNA fragments were sequenced using the GS6 primer.

(7) RT-PCR

Seeds of $T_1$ plants ($T_1$-F03024) from the F03024 line, $T_1$ plants ($T_1$-F01907) from the F01907 line, 6 independent $T_1$-R01907 lines, and wild-type plants were sown in soil. F03024 plants were grown for approximately 6 weeks and F01097 and R01907 plants were grown for 4 weeks.

Rosette leaves from at least 3 different plants per line were harvested and then mRNA was extracted using the Dynabeads mRNA DIRECT Kit (Dynal, Oslo, Norway) according to the instruction manual. For the tissue specificity tests, 5-week-old wild-type Columbia plants grown for 5 weeks after germination were harvested and then mRNA was similarly isolated from corresponding tissues. The mRNA was treated with RQ1Dnase (Promega, Tokyo, Japan) at 37° C. for 1 hour. cDNA was synthesized using the Superscript first-strand synthesis system for RT-PCR (Invitrogen, Carlsbad, U.S.A.) according to the manufacturer's instructions.

RT-PCR was first performed using the following β-tubulin specific primers (Takahashi et al., 2001, Plant Physiol, 126, 731-41) or *Arabidopsis* plasma membrane H+-ATPase (AHA1)-specific primers (Kinoshita et al., 2001, Nature, 414, 656-60) to adjust the ratio of cDNA between wild type and individual lines.

```
TU1:
5'-TTCATATCCAAGGCGGTCAATGTG-3'    (SEQ ID NO: 19)

TU2:
5'-CCATGCCTTCTCCTGTGTACCAA-3'     (SEQ ID NO: 20)

AHA1:
5'-TTCTTCTGGGTGAAGATGTCAGG-3'     (SEQ ID NO: 21)

AHA3:
5'-TGGTTTTAGGAGCAAGACCAGC-3'      (SEQ ID NO: 22)
```

Primers specific to the gene in F03024 are 3024-N and 3024-C:

```
5'-TCAAAGTCTTGCCACTACTAGTCG-3'.   (SEQ ID NO: 31)
```

Primers specific to the gene in F01907 are 1907N: 5'-TGATAGAGAAATGTTTGATCTTCCAT-3' (SEQ ID NO: 23) and 1907C: 5'-TCTTGCTTGTTGGACCGAT-GCTAAG-3' (SEQ ID NO: 24).

PCR was always performed under the following conditions: 94° C. for 30 seconds for denaturation, 60° C. for 30 seconds for annealing, and 72° C. for 120 seconds for elongation.

(8) Gene Expression Analysis by Quantitative Real-Time PCR

RNA was isolated from 1-month-old rosette leaves of $T_2$ R01907 plants derived from one $T_1$ R01907 line using a NucleoSpin RNA Plant kit (MACHEREY-NAGEL GmbH, Duren, Germany). cDNA was synthesized using Superscript first-strand synthesis system (Invitrogen Corp., Carlsbad, U.S.A.) according to the instruction manual.

Real-time PCR analysis was performed using the MX3000P

Multiplex Quantitive PCR System (Promega Corp., Madison, U.S.A.).

SYBR Green Realtime PCR Master Mix (TOYOBO Co. Ltd, Japan) was used for detection of amplified fragments.

Primers used for amplification of reference DNA were ACT2:

```
5'-CTGGATCGGTGGTTCCATTC-3'        (SEQ ID NO: 25)
and

5'-CCTGGACCTGCCTCATCATAC-3'.      (SEQ ID NO: 26)
```

Gene-specific primers used for real-time PCR were RP-1907-2: 5'-CATGCGTCAGGGATAAATCGT-3' (SEQ ID NO: 27) and LP-1907-2: 5'-ACTGTGTGGAAG-GAGCTGGA-3' (SEQ ID NO: 28).

(9) Construction of GFP Fusion Protein and Fluorescence Microscopic Observation

The pF03024S clone was used to amplify the DNA fragment corresponding to the 98 amino acids (sequence) at the N-terminal end of later-described AtPDH1 (cDNA (*Arabidopsis* prokaryotic DEVH box (SEQ ID NO: 38) helicase 1) collected from the F03024 line) using the following primers.

```
attB1-3024N:
                                         (SEQ ID NO: 29)
5'-GGGGACAAGTTTGTACAAAAAAGCAGGCTATGAACACTCTTCCCGTC

GTCT-3' attB2-3024C2:
                                         (SEQ ID NO: 30)
5'-GGGGACCACTTTGTACAAGAAAGCTGGGTCGTCATCGCTATTCCGAA

TTTCA-3'.
```

The amplified DNA fragment was cloned into pGWB5 (Saito et al., 1999, Plant Cell Physiol, 40, 77-87) through mediation by the pDONR-207 vector according to the Gateway instruction manual (Invitrogen, Carlsbad, Calif. U.S.A.).

The resulting construct pGWB3024N98 can over-express the 98 amino acids of the N-terminal region fused with the N-terminal end of a synthetic green fluorescent protein (GFP) gene (Chiu et al., 1996, Curr Biol, 6, 325-30)) under the control of the CaMV 35S transcription promoter (chimeric N98-GFP protein).

pSA701 (provided by Dr. T. Nakagawa, Shimane University, Japan) was used as a negative control construct in which the GFP gene alone was expressed by the 35S promoter.

These plasmids were used for particle bombardment of *Arabidopsis* Col-0 leaves according to standard protocols using the Helios Gene-Gun system (Bio-Rad, Tokyo, Japan).

Individual leaves were observed under a fluorescence microscope (BX 60, Olympus, Tokyo, Japan) using U-MNIBA and U-MWIG filters for GFP fluorescence and chlorophyll fluorescence, respectively.

(10) Electron Microscopic Observance

Rosette leaves of 4-week-old plants (F03024, F01907, and wild-type plants) were fixed with 4% glutaraldehyde, buffered with 20 mM sodium cacodylate at pH 7.0 for 20 hours at 4° C., and then washed with the same buffer for 4 hours at 4° C. Next, they were post-fixed with 2% osmium tetroxide in 20 mM sodium cacodylate buffer (pH 7.0) solution for 20 hours at 4° C. The thus fixed samples were dehydrated through an alcohol series and then embedded in Spurr's resin (Taab, Berkshire, UK). Ultrathin sections were cut with a diamond knife on an ULTRACUT UCT ultramicrotome (Leica, Wien, Austria) and then transferred to Formvar-coated grids. They were double-stained with 4% uranyl acetate for 15 minutes and with a lead citrate solution at room temperature for 10 minutes. After washing with distilled water, the samples were observed using a JEM-1200 EX electron microscope (Jeol, Tokyo, Japan) at 80 kV.

(11) Chlorophyll Content Measurements

Chlorophyll content was measured in two ways.

One method (FIG. 3(*g*)) was performed via direct measurement of the pigment as described in the previous report (Porra et al., 1989, Biochimica et Biophysica Acta, 975, 384-394). Short leaf materials were homogenized in 80% of acetone. The acetone solution was measured using a spectrophotometer (Ultrospec 3000, Pharmacia Biotech, UK) at wavelengths of 663 nm, 645 nm, and 720 nm.

Figure 5:
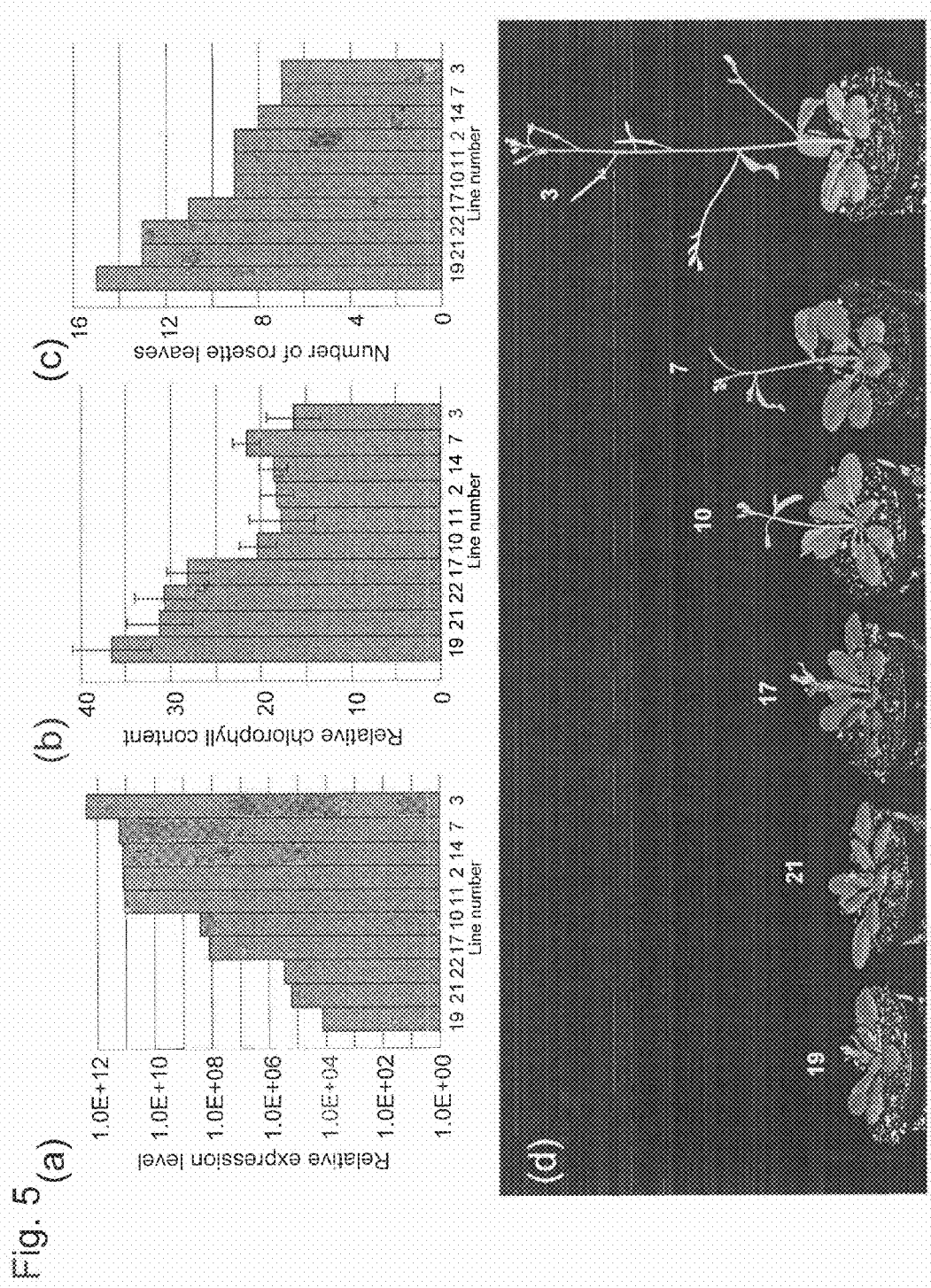
FIG. 5(a) shows the relative expression level of the F01907 line.
FIG. 5(b) shows the relative chlorophyll content of the F01907 line.
FIG. 5(c) shows the number of rosette leaves of the F01907 line.
FIG. 5(d) shows the phenotypes of the F01907 line.

The second method (FIG. 5(*b*)) was performed via determination of the relative content of chlorophyll per unit leaf area using a two wavelength-type handy chlorophyll meter (SPAD-520; Minolta, Tokyo, Japan).

After chlorophyll measurement, the same material was used for the quantitative real-time PCR.

(12) Chlorophyll Fluorescence Measurements

The quantum yield of PSII can be calculated with the following formula:

$$[Pm'=(Fm'-Fs)/Fm'](\text{Genty-parameter})$$

(Fm' and Fs=maximum and steady-state chlorophyll fluorescence in light-adapted leaves). Hence, the chlorophyll fluorescence of leaves of 3-week-old plants was determined at room temperature using a pulse-amplitude-modulated (PAM) fluorometer (MINI-PAM, Walz, Effeltrich, Germany). The results were the means of at least four different leaf measurements.

(13) In Silico Analysis

The BLAST search was carried out using NCBI Blast programs.

Subcellular localization was predicted using TargetP V1.0 (Emanuelsson et al., 2000, J Mol Biol, 300, 1005-16) and ChloroP 1.1 (Emanuelsson et al., 1999, Protein Sci, 8, 978-84).

Multiple alignment was carried out by clustalX (Thompson et al., 1997, Nucleic Acids Res, 25, 4876-82) and Gene-Doc (Nicholas et al., 1997, EMBNEW. NEWS, 4, 14).

A Neighbour-Joining phylogenic tree was constructed using CLUSTALX and TREEVIEW (Page, 1996, Comput Appl Biosci, 12, 357-8).

2. Results (1) Construction of an *Agrobacterium* Expression Library Containing Approximately 10,000 Normalized *Arabidopsis* Full-Length cDNAs Approximately 10,000 independent *Arabidopsis* full-length cDNAs were mixed with the same molar ratio as that used for construction of an *Arabidopsis* full-length cDNA library. These cDNAs were derived from the RIKEN *Arabidopsis* full-length cDNA collection and each cDNA had been sequenced (Seki et al., 2002, Plant J., 31, 279-92). Furthermore, 4 bacterial oncogenes as internal controls, which are known to induce morphological phenotypes and sterility, were mixed. These internal controls can be used as an indicator of cDNA representation in the library, but after transformation into *Arabidopsis*, these oncogenes can be eliminated from the mutant lines in their second generation. Oncogenes: tms1 (Klee et al., 1984, Proc Natl Acad Sci U.S.A., 81, 1728-32); iaaM (Comai et al., 1982, J Bacteriol, 149, 40-6); rolB (Furner et al., 1986, Nature, 319, 422-427); and tmr (Lichtenstein et al., 1984, J Mol Appl Genet, 2, 354-62) were used. These oncogenes are known to have drastic effects on the morphology of many plants. These 4 oncogenes were added to the cDNA mixture at approximately double the molar ratio of each full-length cDNA. It was expected that one oncogene would be encountered in every approximately 7,500 cDNA clones.

After the *Agrobacterium* library (FOX *Agrobacterium* library) was constructed, T-DNA-specific primers were designed to perform PCR on DNAs isolated from randomly chosen *Agrobacterium* colonies. When PCR fragments obtained from 34 *Agrobacterium* colonies were amplified and then subjected to electrophoresis, 20 colonies were found to contain a single-stranded cDNA construct, 11 colonies were found to contain two different cDNA constructs, 1 colony was found to contain three different cDNA constructs, and 2 colonies were found to contain empty vector (FIG. 1(*b*)). Lanes 1, 2, 5, 6, 7, 9, 10, 13, 15, 17, 19, and 22 in FIG. 1(b) showed that a plurality of bands had been amplified (lane M denotes Lambda/HindIII marker).

Furthermore, the average size of these 45 amplified cDNA fragments was 1.4 Kb in the range between 0.3 Kb and 3.0 Kb. When the 45 cDNA fragments were sequenced, all cDNAs were found to be independent of each other (data not shown).

(2) Generation of *Arabidopsis* FOX Lines

For generation of *Arabidopsis* FOX lines, the FOX *Agrobacterium* library was used to transform the *Arabidopsis* Columbia-0 (Col-0) ecotype. After floral dipping, seeds obtained from $T_0$ plants were collected and then selected on hygromycin-containing BAM plates (Nakazawa et al., 2003, Biotechniques, 34, 28-30). Transgenic plants are selected within 1 week after germination with the use of these plates, so that further culturing is not required for selection of hygromycin resistant seedlings. The hygromycin resistant $T_1$ seedlings were transplanted to soil and over 15,000 *Arabidopsis* fertile FOX lines were generated. To confirm the presence of the transgenes, 24 randomly selected plants were analyzed by the Southern method concerning the presence of the marker gene using the hygromycin gene as a probe. All lines were found to contain the hygromycin resistance gene. Furthermore, 2.6 T-DNA inserts were found on average in these *Arabidopsis* FOX lines (data not shown).

(3) Size Distribution and Sequence Difference of Full-Length cDNAs in *Arabidopsis* FOX Lines Full-length cDNAs were incorporated into the expression vector and the size distribution ranged from 0.3 Kb to 3 Kb and was 1.4 Kb on average. If the size distribution was reflected in the *Arabidopsis* FOX lines was examined.

In order to estimate the size distribution and variation of the incorporated cDNAs in these FOX lines, PCR was performed on genomic DNA isolated from randomly selected FOX plants using T-DNA-specific primers. The size distribution of 106 lines was 1.4 Kb on average within the range between 0.3 Kb and 4.2 Kb. FIG. 1(c) shows the size distribution of the 106 RAFL cDNA fragments amplified from the *Arabidopsis* FOX plants, which was obtained via comparison with 277 randomly selected RAFL cDNAs (white bars) in the Lamdba vector. In order to emphasize the similarity of the distribution pattern, values obtained from the Lambda vector were divided by two before plotting and then the results were plotted on the graph.

The average number of PCR fragments amplified from these lines was 1.2 per plant. DNA gel-blot analysis was conducted. Thus, 2.6 T-DNA inserts were found on average per line. However, only an average of 1.2 PCR fragments were collected from FOX plants. Such a low PCR fragment recovery can be explained partially by the presence of the empty vector in the population, but mainly by duplicated T-DNA integration events, such as T-DNA tandem or inverted repeats (De Buck et al., 1999, Plant J, 20, 295-304; De Neve et al., 1997, Plant J, 11, 15-29; Krizkova et al., 1998, Plant J, 16, 673-80).

The average size and range of cDNA distribution were quite similar to those observed in the FOX *Agrobacterium* library and also similar to those observed in 277 randomly selected *Arabidopsis* full-length cDNAs (FIG. 1(c)).

Forty (40) PCR fragments were sequenced, revealing that they were derived from different full-length cDNAs and none of these cDNAs was identical to the bacterial oncogenes added to the cDNA mixture as the internal controls (Table 1).

TABLE 1

Gene annotation of 40 RAFL cDNAs inserted into FOX plants

| Line | RAFL code | P value | MIPS code | Annotation |
| --- | --- | --- | --- | --- |
| F04822 | 06-69-P16 | 3.00E−25 | At1g29390 | unknown protein |
| F04838 | 09-19-I24 | 2.50E−27 | At5g02040 | Sa_e_20 unknown protein |
| F04841 | 05-07-L21 | 1.30E−84 | At2g13360 | fl4o4 alanine-glyoxylate aminotransferase |
| F05137 | ND | 2.80E−32 | At1g26800 | T24P13 unknown protein |
| F05139 | 09-89-F04 | 6.60E−102 | At1g12900 | F13K23 glyceraldehyde 3-phosphatedehydrogenase A, chloroplast precursor, putative |
| F05140 | 04-17-E22 | 4.90E−65 | At5g40370 | mpo 12 glutaredoxin-like protein |
| F05209 | 06-86-D10 | 1.70E−68 | At4g25950 | EN_D_24 vacuolar-type H+-ATPase subunit G3(VHA-G3) |
| F05212 | ND | 6.90E−67 | At1g03020 | F1oo3 putative glutaredoxin |
| F05509 | 21-13-L10 | 5.70E−74 | At1g29395 | F15D2 unknown protein |
| F05535 | 09-23-L13 | 1.00E−72 | At3g52990 | mg_c_20 pyruvate kinase-like protein |
| F05625 | 06-76-K22 | 9.00E−97 | At5g51610 | F9L11 plastid ribosomal protein (PRPL11) |
| F05632 | 04-12-J05 | 1.30E−42 | At1g32990 | K17S15 50s ribosomal protein L11-like |
| F05701 | 09-07-M11 | 2.70E−103 | At4g40070 | MY_D_45 unknown protein |
| F05706 | 06-11-C05 | 2.80E−99 | At4g00895 | T18A10 unknown protein |
| F05735 | 05-14-O11 | 1.00E−24 | At3g50260 | Po-c-22 putative protein |
| F06540 | 08-12-G17 | 6.60E−116 | At5g60360 | muf9 AALP protein |
| F06549 | 09-13-A13 | 1.40E−81 | At2g44100 | f6e13 GDP dissociation inhibitor |
| F06603 | 17-39-M11 | 1.10E−64 | At5g12310 | my_e_31 RING finger-like protein |
| F06603 | 09-34-O21 | 1.80E−103 | At3g09440 | F3L24 heat-shock protein (At-hsc70-3) |
| F06603 | ND | 4.50E−10 | At5g10380 | Wt_e_21 putative protein |
| F06619 | 09-81-K15 | 8.40E−82 | At1g29410 | Phosphoribosylanthranilate isomerase |

TABLE 1-continued

Gene annotation of 40 RAFL cDNAs inserted into FOX plants

| Line | RAFL code | P value | MIPS code | Annotation |
|---|---|---|---|---|
| F06636 | 06-10-F19 | 4.00E−98 | At2g41430 | dehydration-induced protein (ERD15) |
| F06650 | 09-36-H22 | 4.20E−70 | At4g35860 | EN_D_23 GTP-binding protein GB2 |
| F06827 | ND | 9.00E−25 | At5g67190 | K21H1 TINY-like protein |
| F06903 | 06-71-N13 | 3.30E−55 | At4g39090 | MY_D_43 drought-inducible cysteine proteinase RD19A precursor |
| F06909 | ND | 6.10E−20 | At1g03901 | F21M11 unknown protein |
| F06909 | ND | 7.50E−14 | At4g28660 | SR-D-25 photosystem II proteinase RD19A precursor |
| F06913 | 09-67-P06 | 3.70E−123 | At4g24430 | WT_D_35 LG27/30-like gene |
| F07008 | 09-47-K07 | 2.60E−68 | At1g29850 | F1N18 Similar to TF-1 apoptosis related protein 19 |
| F07049 | 04-14-I04 | 9.00E−76 | At5g38430 | MXI10 ribulose bisphosphate carboxylase small chain 1b precursor |
| F07108 | ND | 1.20E−29 | At5g67500 | K9I9 porin-like protein |
| F07703 | ND | 2.00E−37 | At1g70830 | F15H11 unknown protein |
| F07801 | 04-09-O24 | 2.10E−76 | At4g30270 | WU_D_22 xyloglucan endo-1,4-β-D-glucanase precursor |
| F07805 | ND | 1.40E−15 | At1g59740 | F23H11 nitrate transporter NTL1, putative |
| F07818 | 11-02-I02 | 6.10E−61 | At4g25570 | PO_D_20 unknown protein |
| F08101 | 09-19-E06 | 6.40E−60 | At2g16070 | f7h1 unknown protein |
| F08134 | 06-09-G16 | 1.20E−74 | At3g15780 | MSJ11 unknown protein |
| F08151 | 06-11-K21 | 1.20E−80 | At2g20880 | f5h14 AP2 domain transcription factor |
| F08326 | 09-19-L12 | 3.90E−114 | At5g18770 | ch_e_41 putative protein |
| F08509 | 04-20-L08 | 8.20E−77 | At5g66040 | K2A18 senescence-associated protein sen1-like protein; ketoconazole resistance protein-like |

Line: Line name; RAFL code: RAFL number of the corresponding full-length cDNA; ND: not determined; "P value," "MIPS code" and "Annotation" are the results of BLAST searches using the MIPS *Arabidopsis thaliana* Genome Database (http://mips.gsf.de/proj/thal/db/index.html).

(4) Monitoring Phenotypes in the *Arabidopsis* FOX Lines

In the course of generating 15,547 $T_1$ FOX lines, phenotypes (e.g., growth rate, plant color, flowering time, and fertility) were monitored. Thus, 1,487 phenotypically altered lines were collected.

These apparent morphological mutant lines were compared with morphological mutants that had appeared in *Arabidopsis* activation tagged lines. The frequencies of appearance of mutants in the various categories were almost the same as in the activation tagged mutants but the mutants appeared generally with higher efficiencies in the Fox lines (data not shown). This indicates the efficiency of the Fox lines and is mainly due to proper expression of the full-length cDNAs under the control of the strong CaMV promoter and nopaline synthetase (NOS) terminator.

To confirm the heritability of the mutant phenotypes in the $T_2$ generation, 117 pale green mutant lines (Table 2) that had appeared in the $T_1$ generation were grown and then the mutant phenotype in the $T_2$ generation was searched.

TABLE 2

| | Line name | Number of observed plants (O) | Number of plants exhibiting phenotype (P) | T2 phenotype ratio (P/O × 100) |
|---|---|---|---|---|
| 1 | F03430 | 17 | 17 | 100 |
| 2 | F05420 | 17 | 17 | 100 |
| 3 | F05833 | 5 | 4 | 80 |
| 4 | F06017 | 12 | 12 | 100 |
| 5 | F06026 | 8 | 0 | 0 |
| 6 | F06121 | 15 | 0 | 0 |
| 7 | F06405 | 11 | 11 | 100 |
| 8 | F06644 | 10 | 10 | 100 |
| 9 | F07103 | 17 | 17 | 100 |
| 10 | F07146 | 7 | 0 | 0 |
| 11 | F08004 | 9 | 0 | 0 |
| 12 | F08007 | 16 | 16 | 100 |
| 13 | F08211 | 17 | 12 | 70 |
| 14 | F08650 | 17 | 0 | 0 |
| 15 | F08919 | 13 | 0 | 0 |
| 16 | F09751 | 1 | 0 | 0 |
| 17 | F09807 | 4 | 0 | 0 |
| 18 | F10002 | 17 | 0 | 0 |
| 19 | F10116 | 13 | 13 | 100 |
| 20 | F10129 | 17 | 17 | 100 |
| 21 | F10216 | 12 | 10 | 83 |
| 22 | F10223 | 2 | 0 | 0 |
| 23 | F10244 | 16 | 0 | 0 |
| 24 | F10422 | 4 | 4 | 100 |
| 25 | F10428 | 15 | 6 | 40 |
| 26 | F10439 | 17 | 0 | 0 |
| 27 | F10731 | 17 | 17 | 100 |
| 28 | F11005 | 6 | 5 | 83 |
| 29 | F11726 | 9 | 9 | 100 |
| 30 | F12809 | 11 | 0 | 0 |
| 31 | F12929 | 41 | 41 | 100 |
| 32 | F13219 | 12 | 6 | 50 |
| 33 | F13222 | 4 | 3 | 75 |
| 34 | F13602 | 13 | 6 | 46 |
| 35 | F13627 | 17 | 17 | 100 |
| 36 | F14207 | 5 | 3 | 60 |
| 37 | F14344 | 5 | 5 | 100 |

TABLE 2-continued

| | Line name | Number of observed plants (O) | Number of plants exhibiting phenotype (P) | T2 phenotype ratio (P/O × 100) |
|---|---|---|---|---|
| 38 | F14403 | 3 | 3 | 100 |
| 39 | F14442 | 5 | 0 | 0 |
| 40 | F14634 | 40 | 40 | 100 |
| 41 | F14701 | 6 | 5 | 83 |
| 42 | F14702 | 7 | 4 | 57 |
| 43 | F14905 | 15 | 9 | 60 |
| 44 | F15031 | 26 | 18 | 69 |
| 45 | F15113 | 17 | 0 | 0 |
| 46 | F15117 | 16 | 0 | 0 |
| 47 | F15445 | 14 | 14 | 100 |
| 48 | F15649 | 13 | 0 | 0 |
| 49 | F15707 | 17 | 17 | 100 |
| 50 | F15716 | 12 | 0 | 0 |
| 51 | F15836 | 32 | 21 | 65 |
| 52 | F15903 | 9 | 5 | 55 |
| 53 | F16031 | 3 | 0 | 0 |
| 54 | F16128 | 15 | 0 | 0 |
| 55 | F16232 | 13 | 4 | 30 |
| 56 | F16302 | 11 | 11 | 100 |
| 57 | F17212 | 12 | 0 | 0 |
| 58 | F17222 | 12 | 12 | 100 |
| 59 | F17341 | 8 | 7 | 87 |
| 60 | F17620 | 13 | 0 | 0 |
| 61 | F17850 | 17 | 5 | 29 |
| 62 | F17908 | 17 | 0 | 0 |
| 63 | F17918 | 17 | 0 | 0 |
| 64 | F17938 | 17 | 0 | 0 |
| 65 | F18419 | 17 | 17 | 100 |
| 66 | F18625 | 14 | 0 | 0 |
| 67 | F18704 | 14 | 6 | 42 |
| 68 | F18817 | 9 | 9 | 100 |
| 69 | F19419 | 17 | 17 | 100 |
| 70 | F19832 | 17 | 0 | 0 |
| 71 | F19903 | 17 | 0 | 0 |
| 72 | F19934 | 9 | 9 | 100 |
| 73 | F20117 | 1 | 1 | 100 |
| 74 | F20350 | 17 | 17 | 100 |
| 75 | F20610 | 17 | 0 | 0 |
| 76 | F20804 | 1 | 1 | 100 |
| 77 | F21014 | 33 | 18 | 54 |
| 78 | F21129 | 17 | 15 | 88 |
| 79 | F21139 | 43 | 37 | 86 |
| 80 | F21350 | 1 | 1 | 100 |
| 81 | F21617 | 11 | 5 | 45 |
| 82 | F21705 | 17 | 1 | 5 |
| 83 | F22320 | 16 | 8 | 50 |
| 84 | F22723 | 14 | 12 | 85 |
| 85 | F22814 | 17 | 0 | 0 |
| 86 | F22835 | 13 | 0 | 0 |
| 87 | F23218 | 17 | 7 | 41 |
| 88 | F23404 | 57 | 42 | 73 |
| 89 | F23404 | 16 | 1 | 6 |
| 90 | F23607 | 8 | 3 | 37 |
| 91 | F23817 | 17 | 0 | 0 |
| 92 | F24240 | 17 | 10 | 58 |
| 93 | F24737 | 17 | 0 | 0 |
| 94 | F25132 | 17 | 17 | 100 |
| 95 | F25145 | 26 | 26 | 100 |
| 96 | F25344 | 17 | 4 | 23 |
| 97 | F26427 | 17 | 0 | 0 |
| 98 | F26516 | 17 | 10 | 58 |
| 99 | F26615 | 17 | 0 | 0 |
| 100 | F26746 | 17 | 0 | 0 |
| 101 | F26918 | 17 | 15 | 88 |
| 102 | F27141 | 17 | 5 | 29 |
| 103 | F27225 | 17 | 7 | 41 |
| 104 | F27718 | 32 | 17 | 53 |
| 105 | F27904 | 17 | 0 | 0 |
| 106 | F28030 | 16 | 8 | 50 |
| 107 | F28407 | 1 | 0 | 0 |
| 108 | F28409 | 17 | 6 | 35 |
| 109 | F28503 | 17 | 0 | 0 |
| 110 | F28621 | 15 | 5 | 33 |
| 111 | F28909 | 29 | 28 | 96 |
| 112 | F29309 | 17 | 0 | 0 |
| 113 | F29340 | 7 | 7 | 100 |
| 114 | F29739 | 39 | 39 | 100 |
| 115 | F29743 | 17 | 3 | 17 |
| 116 | F30406 | 9 | 2 | 22 |
| 117 | F30503 | 8 | 8 | 100 |

To monitor these phenotypes, 20 seedlings of each line were grown. Although it is difficult to establish clear dominancy from 20 seedlings, 60 lines showed the pale green phenotype (specifically, as shown in Table 2, the number of lines with $T_2$ phenotype ratio of 50% or higher was 60). Moreover, 40 morphological mutants were examined so that 7 lines were found to exhibit the original mutant phenotype. This may be due to suppression of the transgene in the $T_2$ generation or misidentification of the mutants in $T_1$ FOX plants. In particular, dwarf and leaf shape mutants could be caused by environmental stress after transfer from selection plates.

(5) Morphology Caused by Oncogenes

Four (4) oncogenes, tms1, iaaM, rolB, and tmr were mixed with the full-length cDNA library as internal controls. The oncogenes iaaM and tms1 encode tryptophan 2-monooxygenase derived from *P. syringae* and the same derived from *A. tumefaciens*, respectively, and are over-expressed to enhance auxin response (Comai et al., 1982, J Bacteriol, 149, 40-6). The oncogene rolB is derived from *Agrobacterium rhyzogenesis* and involved in sensitivity to auxin. The oncogene tmr is derived from *Agrobacterium tumefaciens* and functions for the biosynthesis of cytokinin. Each of these oncogenes was mixed with full-length cDNA at a ratio of two molar equivalents compared to the other full-length cDNA.

To monitor the expression level and distribution of full-length cDNAs, the appearance of these oncogenes in the *Arabidopsis* FOX lines was examined. Firstly, the morphology of the transgenic plants was monitored for mutants caused by these oncogenes. Only the following two genes were found to actually have a morphological phenotype. Since both tms1 and iaaM cause enhanced auxin response, plants containing these genes were found to have accelerated apical dominance and a compact phenotype (FIG. 2). These morphological features are easily distinguishable very clearly from other morphological mutations. FIG. 2(*a*) shows comparison between an iaaM over-expressing plant and a wild-type (WT) plant grown for the same period. FIG. 2(*b*) shows a photograph showing the iaaM over-expressing plant. FIG. 2(*c*) shows a photograph showing the tms1 over-expressing plant.

Over-expression of tmr caused plant seedlings to die, but over-expression of rolB causes no obvious phenotype. Thirteen (13) tmr1 and iaaM over-expressing mutants were found to be present among 15,547 *Arabidopsis* FOX lines. The apparent number of these mutants was higher than the theoretical value (4 out of 15,000). This may be due to the growth difference of transformed *Agrobacteria* during bacterial culture. One of the advantages of these oncogenes, except for rolB, is that they are not carried over to the next generation because the mutants are sterile.

(6) Characterization of Mutants Due to Plant Early Maturing Gene

Among the above 59 lines that showed the pale green phenotype in the $T_2$ generation, 2 lines were chosen as representatives (F03024 line (the line exhibiting late growth), F01907 line (the early maturing line exhibiting over-expression of the early maturing gene)). F03024 plants exhibited a pale green and late growth phenotype (FIG. 3(a), the phenotype of the F03024 line in the $T_1$ generation). The pale green phenotype was semi-dominant in the $T_2$ generation after self-pollination (FIG. 3(b): F03024 plant from the $T_2$ generation exhibiting the partial pale green phenotype, FIG. 3(c) left: F03024 plant exhibiting pale green stems in the $T_2$ generation, right: wild type segregant of the F03024 line in the $T_2$ generation). F01907 was also isolated as a pale green mutant and its phenotype was dominant in the $T_2$ generation (FIG. 3(e), the phenotype of F01907 in the $T_1$ generation). FIG. 3(g) shows comparison of chlorophyll contents of these lines (in FIG. 3(g), X axis 1: wild-type plants, 2: $T_1$ plants of the F01907 line, 3: $T_1$ plants of the F03024 line, Y axis: relative chlorophyll content).

The introduced full-length cDNAs were recovered by genomic PCR using a T-DNA primer set. A 3.0-Kb cDNA fragment and a 0.8-Kb cDNA fragment were recovered from F03024 and F01907 plants, respectively. The primers were designed to amplify inserted full-length cDNA fragments. The thus recovered cDNA fragments were cloned back into the Agrobacterium Ti plasmid vector and then Arabidopsis (Col-0) plants were transformed using the reconstructed plasmids.

Figure 4:
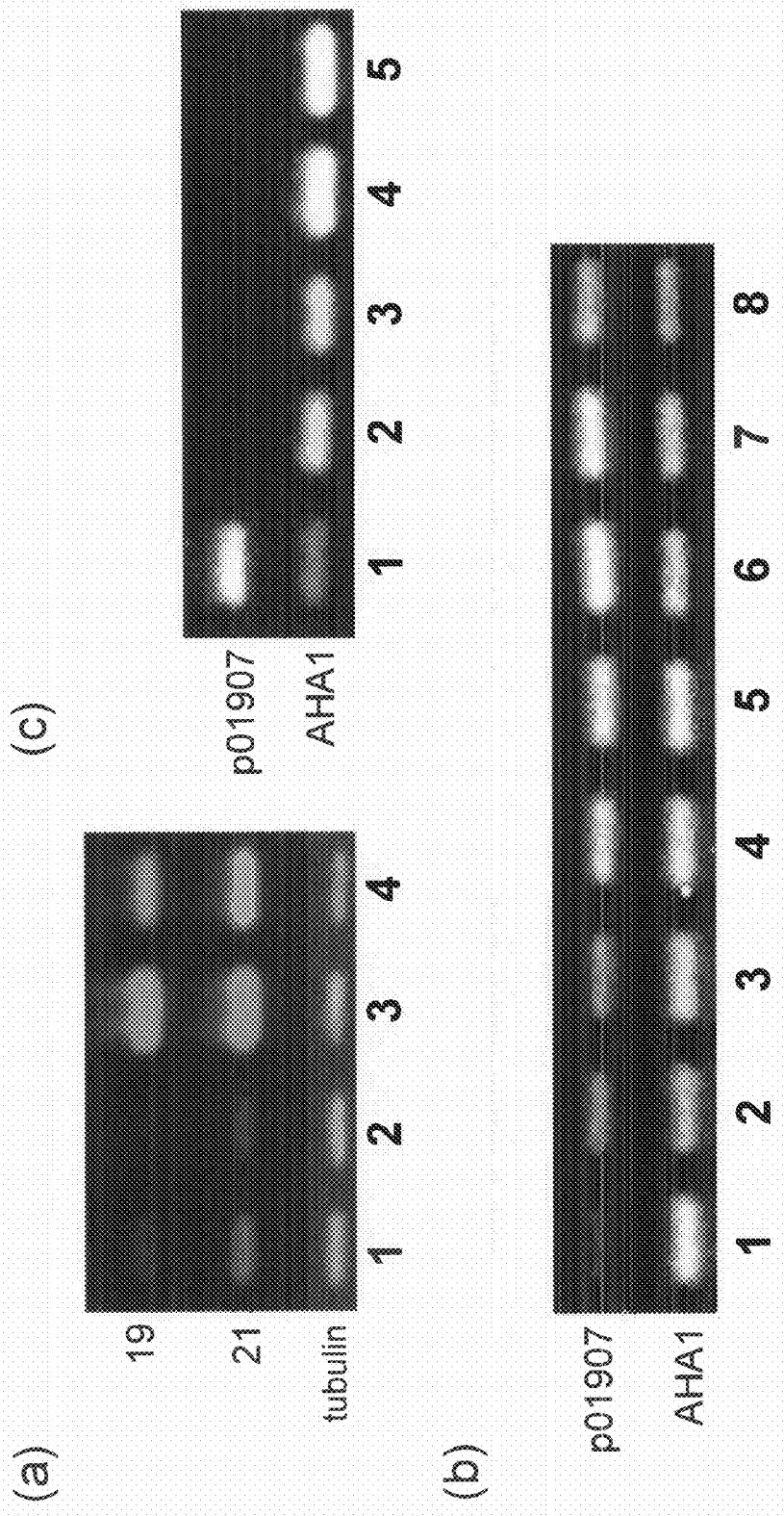
FIG. 4 shows electrophoretic images of genes amplified by RT-PCR.
Figure 8:
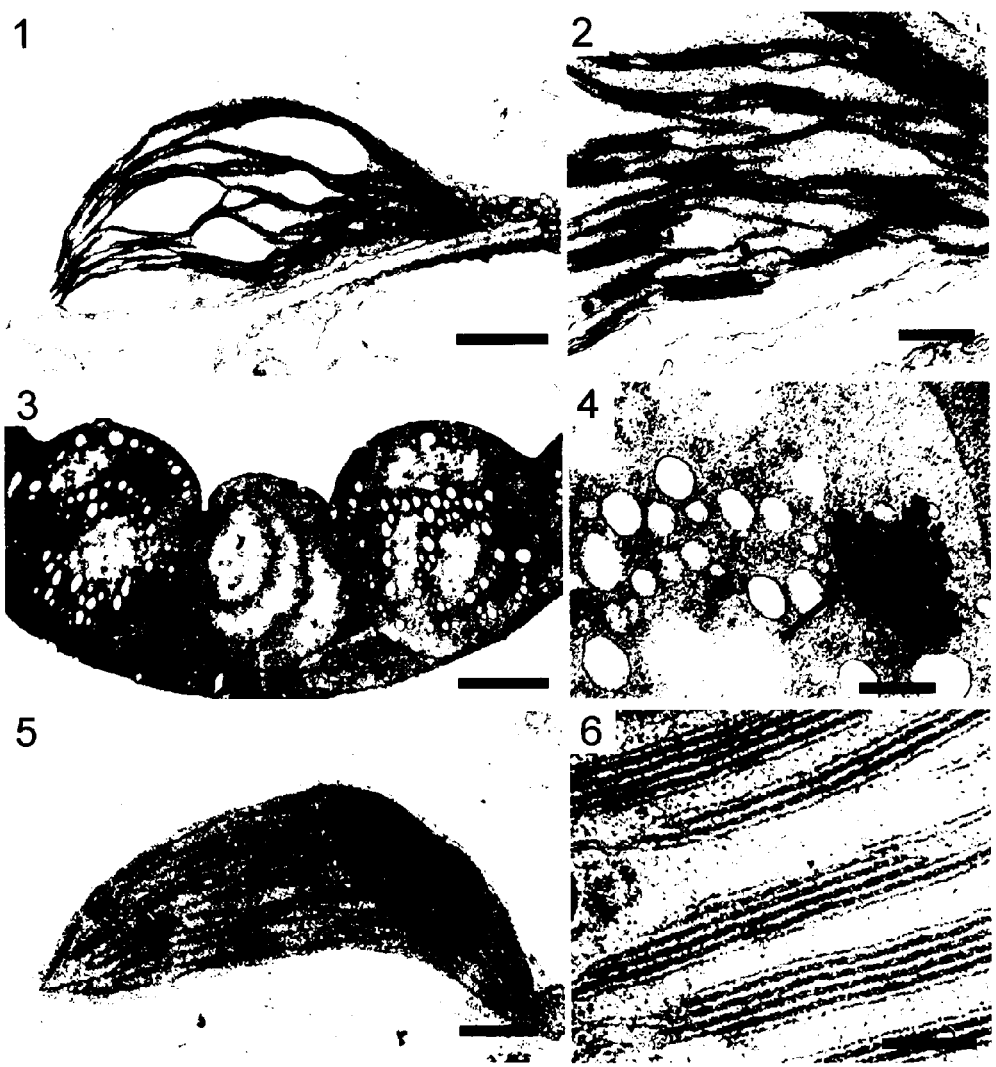
FIG. 8 shows electron microscopic images showing mesophyll cells of the F01907 line and the like. Panels 1 and 2 show electron microscopic images of mesophyll cells of a wild-type plant, panels 3 and 4 show the same of an At1g70070 transgenic plant, and panels 5 and 6 show the same of an At3g55240 transgenic plant.

After growth in soil, 32 out of 48 transgenic plants generated using the cDNA recovered from F03024 showed the pale green and retarded growth phenotype observed in the original F03024 plants (FIG. 3(d), left: an untransformed wild-type plant, right: a wild-type plant transformed with the AtPDH1 gene (described later) exhibiting the pale green phenotype grown for the same period). cDNAs recovered from F03024 were sequenced. The cDNA recovered from F03024 was examined using the NCBI (National center for biotechnology information) database and thus found to be At1g70070 (RIKEN, Japan) Arabidopsis full-length cDNA No. AF387007) and to encode DEVH box (SEQ ID NO: 38) helicase. At1g70070 was over-expressed in F03024 (FIG. 4(a)). DEVH box (SEQ ID NO: 38) helicases are members of a gene family that includes the DEAD (SEQ ID NO: 39) and DEAH (SEQ ID NO: 40) box RNA helicases. The cDNA recovered from F03024 was named AtPDH1 (Arabidopsis prokaryotic DEVH box (SEQ ID NO: 38) helicase 1). There is a report that the tobacco DEAD box (SEQ ID NO: 39) helicase (VDL) targets the chloroplast and regulates chloroplast development (Wang et al., 2000). AtPDH1 has a putative chloroplast target signal in its N-terminal region belonging to a small clade composed of prokaryotic DEAD box (SEQ ID NO: 39) helicases. Intracellular localization of this protein was tested by fusing the N-terminal 98 amino acids to the green fluorescence protein (GFP). Thus, the protein was found to be localized in chloroplasts (FIGS. 9(a) and (b)). When the photosynthetic activity and the chloroplast structure of the pale green leaves of AtPDH1 over-expressing plants were tested, the photosynthetic activity was significantly reduced (FIG. 3(h)). This is due to insufficient development of the chloroplast inner membrane structure (FIG. 8).

Forty seven (47) out of 51 transgenic plants containing the cDNA recovered from F01907 exhibited again the original F01907 phenotype and exhibited the pale green and early flowering phenotype under long day light conditions (FIG. 3(f) left: an untransformed wild-type plant, right: an At3g55240 transgenic plant in the $T_2$ generation exhibiting the pale green and tall height phenotype grown for the same period). The cDNA was sequenced and then examined using the NCBI database, so that it was found to be At3g55240 with unknown functions.

Figure 6:
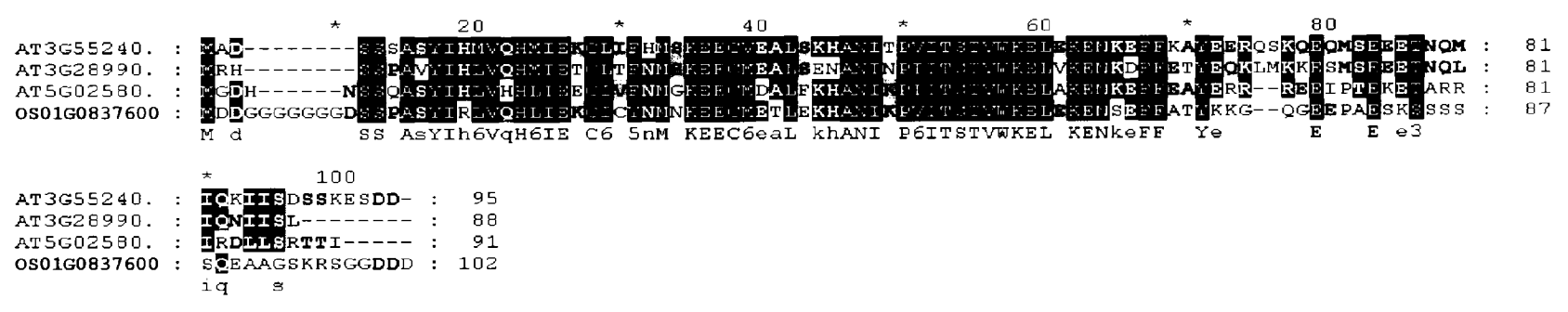
Figure 7:
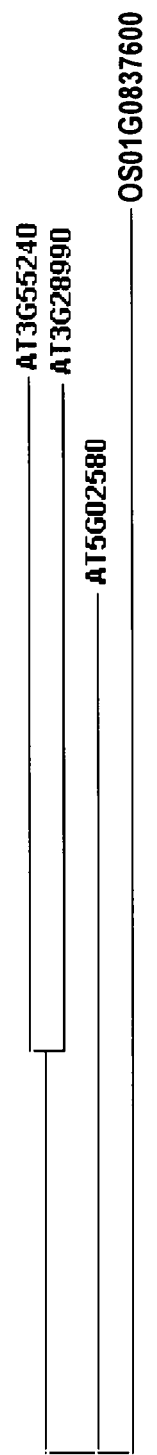
FIG. 7 shows the phylogenic tree of the AT3G55240 protein and the related proteins thereof. AT3G55240, AT3G28990, and AT5G02580 are *Arabidopsis* proteins and OS01G0837600 (old name: P0031D11.2) is a rice EST protein.

F01907 plants exhibited not only the pale green phenotype, but also grew faster and taller than the wild-type plant (FIG. 3(e) and FIG. 3(f)). Since such plant development is reminiscent of that of wild-type plants grown under weak light conditions, this phenotype was designated as "PEL (pseudo-etiolation in light)." The PEL phenotype was caused by the over-expression of the At3g55240 gene with unknown functions (FIG. 4(b), upper bands denote PCR fragments specific to At3g55240 and lower bands denote AHA1 PCR fragments (AHA1: Arabidopsis plasma membrane H+-ATPase) used for loading adjustment, lane 1: wild type Columbia plant, lanes 2-7: $T_2$-R01907 plants exhibiting the pale green phenotype, lane 8: $T_2$-F01907 plant exhibiting the pale green phenotype). In contrast to F03024 plants, these PEL plants have normal photosynthetic activity and normal chloroplast structure (FIG. 3(h), lanes 1-4: 4 independent transgenic plants of At1g70070, lanes 5-7: 3 independent transgenic plants of At3g55240, Y axis: relative photosynthetic activities represented in relation to the wild type, and X axis: individual plants. FIG. 8, electroscopic observation of mesophyll cells: wild type (1 and 2), At1g70070 transgenic plant (3 and 4), and At3g55240 transgenic plant (5 and 6). Arrow indicates aggregation of plastgrobule. Bars 1, 3, and 5 indicate 1 μm. Bars 2, 4, and 6 indicate 200 nm). The At3g55240 gene encodes a small protein (95 amino acids) and has relatively long 3'-UTR (330 bp). Two genes derived from Arabidopsis and genes derived from rice and bean are found to be homologous to this small protein, but such homologous genes are absent in mammals. Thus, these genes were found to be plant specific. FIG. 6 shows the alignment of the AT3G55240 protein and related proteins. AT3G55240, AT3G28990, and AT5G02580 are Arabidopsis proteins. OS01G0837600 (old name: P0031D11.2) is a rice EST protein. Numbers in FIG. 6 indicate the amino acid positions for each protein. FIG. 7 shows the phylogenic tree of the AT3G55240 protein and related proteins. AT3G55240, AT3G28990, and AT5G02580 are Arabidopsis proteins and OS01G0837600 (old name: P0031D11.2) is a rice EST protein. When these genes were subjected to analysis using the subcellular localization prediction program TargetP V1.0, they all showed features characteristic of secretion proteins having N-terminal transmembrane domain and a neighboring cleavage site. However, no protein functions have been reported. Since a knockout line of At3g55240 was not found in the public resource centers, an RNAi construct corresponding to the gene was created and transformed into wild-type Arabidopsis plants. Most of the transgenic plants died at very early developmental stages. Furthermore, no reduction at the transcriptional level of the targeted gene was observed in any remaining transgenic plants. Hence, the knockout phenotype of the At3g55240 gene group may be lethal.

(7) Expression Levels of Transgene and Mutant Phenotype

FOX lines are produced by ectopic expression of individual Arabidopsis full-length cDNA. Thus, the correlation between expression levels of the transgenes and the mutant phenotypes was examined.

The expression levels of At3g55240 in several re-transgenic plants were examined. Expression levels varied from 1.0E+3 times to 1.0E+8 times or more compared with that of the wild type plant (FIG. 5(a) shows the relative expression level of the At3g55240 gene as evaluated by realtime PCR). The chloroplast contents and bolting time (the number of leaves before bolting) of these mutants were examined (FIG. 5(b) shows the relative chloroplast contents of leaves and FIG. 5(c) shows the number of rosette leaves before bolting). A reverse correlation was observed between the expression levels of At3g55240 and chloroplast content and bolting time (FIG. 5(a) to (c)). In FIG. 5(a) to (c), each number on the X axis in each graph denotes the No. of an At3g55240 re-transgenic plant in the T₂ generation. The plant with line No. 19, 21, or 22 is a wild-type segregant showing hygromycin sensitivity. FIG. 5(d) is a photograph showing a T₂ plant with each line No.

These results demonstrated that the mutant morphology is a consequence of the transgene and that the phenotype varies depending on the transgene expression levels. Interestingly, the transcript was preferentially expressed in rosette leaves in wild-type plants (FIG. 4(c), the upper band denotes a PCR fragment (p01907) specific to At3g55240, which was amplified (number of cycles 40) by RT-PCR and the lower band denotes a PCR fragment of AHA1 (*Arabidopsis* plasma membrane H+-ATPase), amplified (number of cycles 28) by RT-PCR and used for loading adjustment. Lane 1: leaves, Lane 2: stems, Lane 3: roots, Lane 4: petals, and Lane 5: seeds).

All publications, patents, and patent applications cited herein are incorporated herein by reference in their entirety.

INDUSTRIAL APPLICABILITY

Advantages can be provided according to the present invention, such that: early maturation of a plant becomes possible via transformation of various plants with a plant early maturing gene, so as to be able to accelerate the timing for harvesting crops and the like; or flower formation can be accelerated by artificially synthesizing the whole or a part of the gene product of such an early maturing gene via peptide synthesis or the like and then adding the product to soil or plants together with water. Moreover, a transgenic plant obtained with the use of the above gene is characterized by increased plant size compared with that of a wild type plant thereof, so that the transgenic plant is useful as an industrial resource, for example.

The early-maturing transgenic plants of the present invention are applicable to agricultural and gardening fields, for example.

The invention claimed is:

1. A transgenic plant whose growth is accelerated compared with a wild-type plant thereof, comprising:
   an isolated nucleic acid molecule that encodes:
   (a) a protein comprising the amino acid sequence shown in SEQ ID NO: 2; or
   (b) a protein comprising an amino acid sequence having 90% or more identity with the amino acid sequence shown in SEQ ID NO: 2 and having activity of accelerating growth of a plant compared with a wild-type plant thereof; or
   an isolated nucleic acid molecule that comprises:
   (c) a DNA molecule comprising the nucleotide sequence shown in SEQ ID NO: 1;
   (d) a DNA molecule comprising a nucleotide sequence having 90% or more identity with the nucleotide sequence shown in SEQ ID NO: 1 and encoding a protein having activity of accelerating growth of a plant compared with a wild-type plant thereof; or
   (e) a DNA molecule hybridizing under stringent conditions to a DNA molecule complementary to a DNA molecule comprising the nucleotide sequence shown in SEQ ID NO: 1 and encoding a protein having activity of accelerating growth of a plant compared with a wild-type plant thereof, wherein the stringent conditions comprise hybridization at 65° C. to 70° C. using 1×SSC and washing at 65° C. to 70° C. using 0.3×SSC, such that the nucleic acid molecule can be expressed,
   wherein the transgenic plant exhibits at least one phenotype selected from the group consisting of an increased plant size, an increased plant height, an earlier flowering, an earlier fructification, an earlier seeding, a lower chloroplast content, and a lower number of rosette leaves before bolting, as compared with a wild-type plant thereof.

2. The transgenic plant according to claim 1, wherein the plant is a dicotyledonous plant or a monocotyledonous plant.

3. The transgenic plant according to claim 1, wherein the nucleic acid molecule is incorporated in the plant genome.

4. The transgenic plant according to claim 1, wherein the protein further has activity of increasing the size of a plant compared with that of a wild-type plant thereof.

5. A tissue, cell or seed, which is derived from the transgenic plant according to claim 1, wherein the seed comprises the nucleic acid molecule contained in the parent transgenic plant.

6. A method for producing a transgenic plant whose growth is accelerated compared with a wild-type plant thereof, the method comprising introducing an isolated nucleic acid molecule into a plant tissue or cell and regenerating a plant, wherein
   (a) the nucleic acid molecule encodes the protein comprising SEQ ID NO: 2;
   (b) the nucleic acid molecule encodes a protein comprising an amino acid sequence having 90% or more identity with SEQ ID NO: 2 and having activity of accelerating growth of a plant compared with a wild-type plant thereof;
   (c) the nucleic acid molecule comprises SEQ ID NO: 1;
   (d) the nucleic acid molecule comprises a sequence having 90% or more identity with SEQ ID NO:1 and encodes a protein having activity of accelerating growth of a plant compared with a wild-type plant thereof; or
   (e) the nucleic acid molecule hybridizes under stringent conditions to a nucleic acid molecule that is complementary to SEQ ID NO:1 and encodes a protein having activity of accelerating growth of a plant compared with a wild-type plant thereof, wherein the stringent conditions comprise hybridization at 65° C. to 70° C. using 1×SSC and washing at 65° C. to 70° C. using 0.3×SSC, and
   wherein the nucleic acid molecule is expressed and wherein the transgenic plant exhibits at least one phenotype selected from the group consisting of an increased plant size, an increased plant height, an earlier flowering, an earlier fructification, an earlier seeding, a lower chloroplast content, and a lower number of rosette leaves before bolting, as compared with a wild-type plant thereof.

7. The method according to claim 6, wherein the nucleic acid molecule is introduced into the plant in a recombinant vector comprising the nucleic acid molecule.

8. A method for accelerating growth of a plant compared with a wild-type plant thereof, the method comprising introducing and overexpressing an isolated nucleic acid molecule in the plant, thereby inducing accelerated growth of the plant compared with a wild-type plant thereof,
wherein
   (a) the nucleic acid molecule encodes the protein comprising SEQ ID NO: 2;
   (b) the nucleic acid molecule encodes a protein comprising an amino acid sequence having 90% or more identity with SEQ ID NO: 2 and having activity of accelerating growth of a plant compared with a wild-type plant thereof;
   (c) the nucleic acid molecule comprises SEQ ID NO: 1;
   (d) the nucleic acid molecule comprises a sequence having 90% or more identity with SEQ ID NO: 1 and encodes a protein having activity of accelerating growth of a plant compared with a wild-type plant thereof; or
   (e) the nucleic acid molecule hybridizes under stringent conditions to a nucleic acid molecule that is complementary to SEQ ID NO: 1 and encodes a protein having activity of accelerating growth of a plant compared with a wild-type plant thereof, wherein the stringent conditions comprise hybridization at 65° C. to 70° C. using 1×SSC and washing at 65° C. to 70° C. using 0.3×SSC, and
wherein the plant exhibits at least one phenotype selected from the group consisting of an increased plant size, an increased plant height, an earlier flowering, an earlier fructification, an earlier seeding, a lower chloroplast content, and a lower number of rosette leaves before bolting, as compared with a wild-type plant thereof.

9. A method for increasing the size of a plant, the method comprising introducing and overexpressing an isolated nucleic acid molecule in the plant, thereby inducing an increase in plant size compared with that of a wild-type plant thereof, wherein
   (a) the nucleic acid molecule encodes the protein comprising SEQ ID NO: 2;
   (b) the nucleic acid molecule encodes a protein comprising an amino acid sequence having 90% or more identity with SEQ ID NO: 2 and having activity of accelerating growth of a plant compared with a wild-type plant thereof;
   (c) the nucleic acid molecule comprises SEQ ID NO:1;
   (d) the nucleic acid molecule comprises a sequence having 90% or more identity with SEQ ID NO:1 and encodes a protein having activity of accelerating growth of a plant compared with a wild-type plant thereof; or
   (e) the nucleic acid molecule hybridizes under stringent conditions to a nucleic acid molecule that is complementary to SEQ ID NO: 1 and encodes a protein having activity of accelerating growth of a plant compared with a wild-type plant thereof; wherein the stringent conditions comprise hybridization at 65° C. to 70° C. using 1×SSC and washing at 65° C. to 70° C. using 0.3×SSC,
wherein the plant exhibits a phenotype of an increased plant size as compared with a wild-type plant thereof.

10. The transgenic plant according to claim 1, wherein
   (a) the protein comprises an amino acid sequence having 95% or more identity with the amino acid sequence shown in SEQ ID NO:2 and has activity of accelerating growth of a plant compared with a wild-type plant thereof; and or
   (b) the DNA molecule comprises a nucleotide sequence having 95% or more identity with the nucleotide sequence shown in SEQ ID NO: 1 and encodes a protein having activity of accelerating growth of a plant compared with a wild-type plant thereof.

11. The method according to claim 6, wherein
   (a) the nucleic acid molecule comprises a sequence having 95% or more identity with SEQ ID NO: 1 and encodes a protein having activity of accelerating growth of a plant compared with a wild-type plant thereof.

12. The method according to claim 8, wherein
   (a) the nucleic acid molecule encodes a protein comprising an amino acid sequence having 95% or more identity with SEQ ID NO: 2 and has activity of accelerating growth of a plant compared with a wild-type plant thereof; or
   (b) the nucleic acid molecule comprises a sequence having 95% or more identity with SEQ ID NO: 1 and encodes a protein having activity of accelerating growth of a plant compared with a wild-type plant thereof.

13. The method according to claim 9, wherein
   (a) the nucleic acid molecule encodes a protein comprising an amino acid sequence having 95% or more identity with SEQ ID NO: 2 and has activity of accelerating growth of a plant compared with a wild-type plant thereof; or
   (b) the nucleic acid molecule comprises a sequence having 95% or more identity with SEQ ID NO: 1 and encodes a protein having activity accelerating growth of a plant compared with a wild-type plant thereof.

* * * * *

```
                         SEQUENCE LISTING

<160> NUMBER OF SEQ ID NOS: 40

<210> SEQ ID NO 1
<211> LENGTH: 670
<212> TYPE: DNA
<213> ORGANISM: Arabidopsis thaliana

<400> SEQUENCE: 1
aaagaagact ctcttttaag tttgggtgtt aattctaggg tttccattaa caatggcaga      60
ttcttcttct gcttcttaca ttcacatggt gcagcacatg atagagaaat gtttgatctt     120
ccatatgagc aaagaagagt gtgtggaagc tctctctaag catgcaaaca tcactcctgt     180
catcacctct actgtgtgga aggagctgga gaaagagaac aaggaattct tcaaggcgta     240
tgaggagagg caaagcaaac aagagcaaat gtcggaggaa gagacaaacc agatgatcca     300
gaagattatc tcggattcat ctaaagaatc cgacgactga tcgcgatgtt cgatcgttag     360
atttcgaaaa ccttatagtt tatatatatg aatctcatga aaacgattta tccctgacgc     420
atgcatgttt ataagtaaat cgttttttca tcttagcatc ggtccaacaa gcaagacagc     480
aaaaaaagga gtgatgacac tctttttggt acgttatacg tacgtggtcc acataatatt     540
gcctctgttt aattatatat aatgaaacgg acgctagctc atacatggat cgatggtgtg     600
gtgttttaat tgaatgtatc gtgtgtatat attttcaaat aaactattta tttcgggttt     660
tggtcacctt                                                            670

<210> SEQ ID NO 2
<211> LENGTH: 95
<212> TYPE: PRT
<213> ORGANISM: Arabidopsis thaliana

<400> SEQUENCE: 2

Met Ala Asp Ser Ser Ser Ala Ser Tyr Ile His Met Val Gln His Met
1               5                   10                  15

Ile Glu Lys Cys Leu Ile Phe His Met Ser Lys Glu Glu Cys Val Glu
            20                  25                  30

Ala Leu Ser Lys His Ala Asn Ile Thr Pro Val Ile Thr Ser Thr Val
        35                  40                  45

Trp Lys Glu Leu Glu Lys Glu Asn Lys Glu Phe Phe Lys Ala Tyr Glu
    50                  55                  60
```

Glu Arg Gln Ser Lys Gln Glu Gln Met Ser Glu Glu Thr Asn Gln
65                  70                  75                  80

Met Ile Gln Lys Ile Ile Ser Asp Ser Ser Lys Glu Ser Asp Asp
            85                  90                  95

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
agaggccaaa tcggccatgt cagcttcacc tctcctt                              37

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agaggccctt atggccctaa tttctagtgc ggtagttat                            39

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agaggccaaa tcggccatgt atgaccattt taattcaccc                           40

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agaggccctt atggccctaa tagcgatagg aggcgttg                             38

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcctctagag gccaaatcgg ccatggatcc caaattgcta ttcct                     45

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgatctagag gcccttatgg ccttaggctt ctttcttcag gttta            45

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agaggccaaa tcggccatgg acctgcatct aattttcg                    38

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agaggccctt atggccccta atacattccg aacggatga                   39

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atgaaaaagc ctgaactcac cg                                     22

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tcgagagcct gcgcgacg                                          18

<210> SEQ ID NO 13
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggggacaagt ttgtacaaaa aagcaggctc tagaggccct tatggccg         48

<210> SEQ ID NO 14
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

```
ggggaccact ttgtacaaga aagctgggtt cgagttaatt aaattaatcc ccc        53
```

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
acattctaca actacatcta gagg                                        24
```

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
cggccgcccc ggggatc                                                17
```

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

```
tcgcgttaac gctagcatgg atctc                                       25
```

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

```
gtaacatcag agattttgag acac                                        24
```

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

```
ttcatatcca aggcggtcaa tgtg                                        24
```

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

```
ccatgccttc tcctgtgtac caa                                         23
```

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ttcttctggg tgaagatgtc agg                                           23

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tggttttagg agcaagacca gc                                            22

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgatagagaa atgtttgatc ttccat                                        26

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcttgcttgt tggaccgatg ctaag                                         25

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ctggatcggt ggttccattc                                               20

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cctggacctg cctcatcata c                                             21

```
<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
catgcgtcag ggataaatcg t                                              21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
actgtgtgga aggagctgga                                                20

<210> SEQ ID NO 29
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggggacaagt ttgtacaaaa aagcaggcta tgaacactct tcccgtcgtc t             51

<210> SEQ ID NO 30
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggggaccact ttgtacaaga aagctgggtc gtcatcgcta ttccgaattt ca            52

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tcaaagtctt gccactacta gtcg                                           24

<210> SEQ ID NO 32
<211> LENGTH: 293
<212> TYPE: DNA
<213> ORGANISM: Arabidopsis thaliana

<400> SEQUENCE: 32
tggttgtagc aaaatatata atagaaatga gacactcttc tcccgctgta tacattcatc    60
tggtgcaaca catgatagag acatgtttga cctttaacat gagcaaagag gaatgcatgg   120
aagctctctc agagaatgca aacatcaatc ccatcatcac gtccactgtt tggaaggagc   180
tggttaaaga gaacaaggac ttcttgaga cgtacgagca gaagcttatg aaaaaggaat    240
```
caatgtcgga ggaggagaca aaccaattaa ttcagaacat catctctttg tga    293

<210> SEQ ID NO 33
<211> LENGTH: 88
<212> TYPE: PRT
<213> ORGANISM: Arabidopsis thaliana

<400> SEQUENCE: 33

Met Arg His Ser Ser Pro Ala Val Tyr Ile His Leu Val Gln His Met
1               5                   10                  15

Ile Glu Thr Cys Leu Thr Phe Asn Met Ser Lys Glu Glu Cys Met Glu
            20                  25                  30

Ala Leu Ser Glu Asn Ala Asn Ile Asn Pro Ile Ile Thr Ser Thr Val
        35                  40                  45

Trp Lys Glu Leu Val Lys Glu Asn Lys Asp Phe Phe Glu Thr Tyr Glu
    50                  55                  60

Gln Lys Leu Met Lys Lys Glu Ser Met Ser Glu Glu Thr Asn Gln
65                  70                  75                  80

Leu Ile Gln Asn Ile Ile Ser Leu
            85

<210> SEQ ID NO 34
<211> LENGTH: 722
<212> TYPE: DNA
<213> ORGANISM: Arabidopsis thaliana

<400> SEQUENCE: 34
cgggtcttgt agcgttttat atatattttc acctgccttt cttctcccat ccatcatcat    60
atctctctct aatttctctc cgtataacac aaactactct ttaataagta tttatgggtg   120
atcataatag ctcgcaagct tcttacatcc atttggtgca tcatttgata gaagaatgta   180
tagtattcaa catgggcaaa gaagagtgta tggatgctct gttcaagcat gctaatatta   240
agcctatcat cacttccaca gtgtggaaag agctagcgaa agagaacaaa gagttcttcg   300
aggcatacga gaagacga gaagaaatac cgaccgagaa agagacagct cgaagaatcc   360
gtgatttgct ttcacgaact acaatctaag atcatgacac ctacttttac ttacatatac   420
atacactcat ctatattacc ataggcatgt gtgtgtatat gtatgatccg acgattctat   480
atatactctt tagacaattt gtattataat cttcattagg aaatgaataa ttcacctttg   540
gggaaatctc ttttcagct agtttaaaa tcgttatgat ttatttgctc ttttcacgt   600 tatgatttat ttgcgtatta cttttctta cgttatgatt tatttgtaag ttaccaattg   660
gatcttaacc attttcaatg tctaaacaat gttattggag cataatatac ctgtctttgt   720
gt   722

<210> SEQ ID NO 35
<211> LENGTH: 91
<212> TYPE: PRT
<213> ORGANISM: Arabidopsis thaliana

<400> SEQUENCE: 35

Met Gly Asp His Asn Ser Ser Gln Ala Ser Tyr Ile His Leu Val His
1               5                   10                  15

His Leu Ile Glu Glu Cys Ile Val Phe Asn Met Gly Lys Glu Glu Cys
            20                  25                  30

Met Asp Ala Leu Phe Lys His Ala Asn Ile Lys Pro Ile Ile Thr Ser
        35                  40                  45

Thr Val Trp Lys Glu Leu Ala Lys Glu Asn Lys Glu Phe Phe Glu Ala

```
                50                  55                  60
Tyr Glu Arg Arg Arg Glu Glu Ile Pro Thr Glu Lys Glu Thr Ala Arg
 65                  70                  75                  80

Arg Ile Arg Asp Leu Leu Ser Arg Thr Thr Ile
                 85                  90

<210> SEQ ID NO 36
<211> LENGTH: 680
<212> TYPE: DNA
<213> ORGANISM: Oryza sativa

<400> SEQUENCE: 36
gttggtcgat cactccatcg atccatcgat cgatcgctag ctactcgccg tcgtcgaccg      60
gtcgatccgc cattagcgag ctgcaaggct ctctcgctta taaatcttcc gagtaggcaa     120
gcctcaatcg atccgagagt tggtcgttg atcgagctga tcgatcgacc ggtgagtggt     180
gcgtggtgtg cggccatgga cgacggcggc ggcggcggcg gcggcgactc gtcgccggct     240
tcgtacatca gattggtgca gcatctgatc gagaagtgca tctgctacaa catgaacaag     300
gaggaatgca tggagacgct ggagaagcac gccaacatca gcccgtcat cacctccacc     360 gtgtggaagg agcttgagaa ggagaacagc gagttcttcg ccacgtacaa gaagggccaa     420
ggagaggaac cagcggagag caagagcagt agttcttcac aggaagctgc tggttccaag     480
agatcaggcg gagacgacga ctaggtgcat gcatggcacc cacgagagag ggggctactt     540
gtacagtagg atatccatca agtcgtagta cctcgtactg tcttacatct agctgttcat     600
agtacatagc gtatagtagt aatgtagccg ttattatgta cgttttgccc cgaaaataat     660
taagattcgg attcgcagct                                                 680

<210> SEQ ID NO 37
<211> LENGTH: 102
<212> TYPE: PRT
<213> ORGANISM: Oryza sativa

<400> SEQUENCE: 37

Met Asp Asp Gly Gly Gly Gly Gly Gly Asp Ser Ser Pro Ala Ser
 1               5                  10                  15

Tyr Ile Arg Leu Val Gln His Leu Ile Glu Lys Cys Ile Cys Tyr Asn
                 20                  25                  30

Met Asn Lys Glu Glu Cys Met Glu Thr Leu Glu Lys His Ala Asn Ile
             35                  40                  45

Lys Pro Val Ile Thr Ser Thr Val Trp Lys Glu Leu Glu Lys Glu Asn
         50                  55                  60

Ser Glu Phe Phe Ala Thr Tyr Lys Lys Gly Gln Gly Glu Glu Pro Ala
 65                  70                  75                  80

Glu Ser Lys Ser Ser Ser Ser Gln Glu Ala Ala Gly Ser Lys Arg
                 85                  90                  95

Ser Gly Gly Asp Asp Asp
            100

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38
```

```
Asp Glu Val His
1

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Glu Ala Asp
1

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Glu Ala His
1
```